United States Patent
Contorni et al.

(10) Patent No.: US 9,855,324 B2
(45) Date of Patent: Jan. 2, 2018

(54) IMMUNOGENIC COMPOSITIONS

(71) Applicant: GlaxoSmithKline Biologicals SA, Rixensart (BE)

(72) Inventors: Mario Contorni, Siena (IT); Guido Grandi, Segrate (IT); Domenico Maione, Siena (IT); Immaculada Margarit Y Ros, Siena (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 14/424,362

(22) PCT Filed: Oct. 3, 2013

(86) PCT No.: PCT/EP2013/070647
§ 371 (c)(1),
(2) Date: Feb. 26, 2015

(87) PCT Pub. No.: WO2014/053607
PCT Pub. Date: Apr. 10, 2014

(65) Prior Publication Data
US 2015/0224185 A1    Aug. 13, 2015

Related U.S. Application Data

(60) Provisional application No. 61/744,880, filed on Oct. 3, 2012, provisional application No. 61/799,123, filed on Mar. 15, 2013.

(51) Int. Cl.
| | |
|---|---|
| *A61K 39/09* | (2006.01) |
| *A61K 39/00* | (2006.01) |
| *A61K 39/05* | (2006.01) |
| *A61K 39/08* | (2006.01) |
| *A61K 39/02* | (2006.01) |
| *A61K 39/13* | (2006.01) |
| *A61K 39/12* | (2006.01) |
| *C12N 7/00* | (2006.01) |
| *A61K 9/00* | (2006.01) |
| *A61K 47/64* | (2017.01) |

(52) U.S. Cl.
CPC ......... *A61K 39/092* (2013.01); *A61K 9/0019* (2013.01); *A61K 39/0018* (2013.01); *A61K 39/05* (2013.01); *A61K 39/08* (2013.01); *A61K 39/099* (2013.01); *A61K 39/12* (2013.01); *A61K 39/13* (2013.01); *A61K 47/646* (2017.08); *C12N 7/00* (2013.01); *A61K 2039/55* (2013.01); *A61K 2039/55505* (2013.01); *A61K 2039/6037* (2013.01); *A61K 2039/70* (2013.01); *C12N 2770/32334* (2013.01); *C12N 2770/32634* (2013.01)

(58) Field of Classification Search
None
See application file for complete search history.

(56) References Cited

U.S. PATENT DOCUMENTS

| | | | |
|---|---|---|---|
| 5,057,540 A | 10/1991 | Kensil et al. | |
| 6,426,074 B1 * | 7/2002 | Michel | C07K 14/315 424/184.1 |
| 8,029,798 B2 | 10/2011 | Leroy | |
| 2004/0202668 A1 | 10/2004 | Boutriau et al. | |
| 2009/0043077 A1 * | 2/2009 | Berti | A61K 39/09 530/363 |
| 2010/0150943 A1 | 6/2010 | Grandi et al. | |
| 2013/0273091 A1 | 10/2013 | Berti et al. | |
| 2015/0224204 A1 | 8/2015 | Grandi et al. | |
| 2015/0283232 A1 | 10/2015 | Berti et al. | |

FOREIGN PATENT DOCUMENTS

| | | | |
|---|---|---|---|
| EP | 0109942 | 5/1984 | |
| IT | WO 2012035519 A1 * | 3/2012 | ........ A61K 39/092 |
| WO | 1994/06467 | 3/1994 | |
| WO | 96/11711 | 4/1996 | |
| WO | 96/33739 | 10/1996 | |
| WO | 96/40242 | 12/1996 | |
| WO | 96/40795 | 12/1996 | |
| WO | 99/24578 | 5/1999 | |
| WO | 99/36544 | 7/1999 | |
| WO | 99/52549 | 10/1999 | |
| WO | 99/57280 | 11/1999 | |
| WO | 00/07621 | 2/2000 | |
| WO | 00/23105 | 4/2000 | |
| WO | 2000/22430 | 4/2000 | |
| WO | 01/21152 | 3/2001 | |

(Continued)

OTHER PUBLICATIONS

Rodewald, et al., Neonatal Mouse Model of Group B Streptococcal Infection, J Infect Dis, 166(3): 635-639 (1992).
Rosenqvist, et al., Effect of Aluminium Hydroxide and Meningococcal Serogroup C Capsular Polysaccharide on the Immunogenicity and Reactogenicity of a Group B Neisseria meningitidis Outer Membrane Vesicle Vaccine, Dev Biol Stand 92:323-333 (1998).
Schutze et al, Carrier-Induced Epitopic Suppression, A Major Issue for Future Synthetic Vaccines, J Immunol 135 (4):2319-2322 (1985).
Tettelin et al., Complete Genome Sequence of Neisseria meningitidis Serogroup B Strain MC58, Science 287:1809-1815 (2000).
Wang, et al., Construction of designer glycoconjugate vaccines with size-specific oligosaccharide antigens and site-controlled coupling, Vaccine 21(11-12):1112-1117 (2003).

(Continued)

*Primary Examiner* — Brian J Gangle
(74) *Attorney, Agent, or Firm* — Virginia G. Campen

(57) ABSTRACT

The invention provides an immunogenic composition comprising one or more GBS conjugates and one or more antigens selected from: a) cellular or acellular pertussis antigen, b) a tetanus toxoid, c) a diphtheria toxoid and d) an inactivated polio virus antigen, wherein each GBS conjugate is a group B *streptococcus* capsular saccharide conjugated to a carrier protein. The invention also provides a method for raising an immune response in a patient, comprising the step of administering to the patient a composition of the invention.

15 Claims, 17 Drawing Sheets

(56) References Cited

FOREIGN PATENT DOCUMENTS

| | | |
|---|---|---|
| WO | 01/21207 | 3/2001 |
| WO | 2001/52885 | 7/2001 |
| WO | 2002/34771 | 5/2002 |
| WO | 2003/093306 | 11/2003 |
| WO | 2004/018646 | 3/2004 |
| WO | 2006/050341 | 5/2006 |
| WO | 2006/069200 | 6/2006 |
| WO | 2006082527 | 8/2006 |
| WO | 2006082530 | 8/2006 |
| WO | 2008/028956 | 3/2008 |
| WO | 2008/028957 | 3/2008 |
| WO | 2008/127179 | 10/2008 |
| WO | 2009/010877 | 1/2009 |
| WO | 2009/081276 | 7/2009 |
| WO | 2009101403 | 8/2009 |
| WO | 2012/035519 | 3/2012 |
| WO | 2013/088378 | 6/2013 |

OTHER PUBLICATIONS

Wessels, et al., A model of high-affinity antibody binding to type III group B Streptococcus capsular polysaccharide, PNAS 84:9170-9174 (1987).
Wessels et al., Isolation and Characterization of Type IV Group B Streptococcus Capsular Polysaccharide, Infect & Immun 57(4):1089-1094 (1989).
Wessels, et al., Immunogenicity in Animals of a Polysaccharide-Protein Conjugate Vaccine against Type III gGroup B Streptococcus, J Clin Invest 86(5):1428-1433 (1990).
Wessels, et al., Stimulation of Protective Antibodies against Type Ia and Ib Group B Streptococci by a Type Ia Polysaccharide-Tetanus Toxoid Conjugate Vaccine, Infect & Immun 61(11): 4760-4766 (1993).
Wessels, et al., Immunogenicity and Protective Activity in Animals of a Type V Group B Streptococcal Polysaccharide-Tetanus Toxoid Conjugate Vaccine, J Infect Dis 171(4):879-884 (1995).
International Search Report dated Feb. 17, 2014 for Priority Application PCT/EP2013/070647 of Present Case, U.S. Appl. No. 14/424,362.
International Search Report dated Feb. 13, 2014 for Priority Application PCT/EP2013/070656 of Related Case, U.S. Appl. No. 14/662,429.
International Search Report dated Feb. 13, 2014 for Priority Application PCT/EP2013/070656 of Related Case, U.S. Appl. No. 14/424,370.
Adderson, et al., Subtractive Hybridization Identifies a Novel Predicted Protein Mediating Epithelial Cell Invasion by Virulent Serotype III Group B Streptococcus agalactiae, Infect & Immun, 71:12: 6857-6863 (2003).
Baker, et al., Safety and Immunogenicity of Capsular Polysaccharide-Tetanus Toxoid Conjugate Vaccines for Group B Steptococcal Types Ia and Ib, J Infect Dis, 179(1): 142-150 (1999).
Baker, et al., Use of Capsular Polysaccharide-Tetanus Toxoid Conjugate Vaccines for Type II Group B Steptococcus in Healthy Women, J Infect Dis 182(4): 1129-1138 (2000).
Baker, et al., Immunization of pregnant women with group B streptococcal type III capsular polysaccharide-tetanus toxoid conjugate vaccine, Vaccine 21(24): 3468-3472 (2003).
Baker, et al., Safety and Immunogenicity of a Bivalent Group B Streptococcal Conjugate Vaccine for Serotypes II and III, J Infect Dis 188(1): 66-73 (2003).
Baker, et al., Immune Response in Healthy Women to 2 Different Group B Streptoccal Type V Capsular Polysaccharide-Protein Conjugate Vaccines, J Infect Dis 189(6): 1103-1112 (2004).
Baker, et al., Dose-response to type V group B streptococcal polysaccharide-tetanus toxoid conjugate vaccine in healthy adults, Vaccine 25(1): 55-63 (2007).
Barington et al., Non-Epitope-Specific Suppression of the Antibody Response to Haemophilus influenzae Type b Conjugate Vaccines by Preimmunization with Vaccine Components, Infect & Immun 61(2): 432-438 (1993).
Barington et al., Opposite Effects of Actively and Passively Acquired Immunity to the Carrier on Responses of Human Infants to a Haemophilus influenzae Type b Conjugate Vaccine, Infect & Immun, 62(1): 9-14 (1994).
Bjune et al., Effect of outer membrane vesicle vaccine against group B meningococcal disease in Norway, (1991), LANCET 338(8775): 1093-1096.
Brigtsen, et al., Induction of Cross-Reactive Antibodies by Immunization of Healthy Adults with Types Ia and Ib Group B Streptococcal Polysaccharide—Tetanus Toxoid Conjugate Vaccines, (2002), J Infect Dis 185:1277-1284.
Burrage et al., Effect of Vaccination with Carrier Protein on Response to Meningococcal C Conjugate Vaccines and Value of Different Immunoassays as Predictors of Protection, Infect & Immun, 70(9): 4946-4954 (2002).
Costantino et al., Development and phase 1 clinica testing of a conjugate vaccine against meningococcus A and C, Vaccine, 10(10): 691-698 (1992).
Dagan et al., Infect & Immun, Reduced Response to Multiple Vaccines Sharing Common Protein Epitopes That Are Administered Simultaneously to Infants, 66(5): 2093-2098 (1998).
Dale, Group A Streptococcal Vaccines, Infect Dis Clinics N America, 13(1): 227-243 (1999).
Dick and Beurret, Glycoconjugates of Bacterial Carbohydrate Antigens. A Survey and Consideration of Design and Preparation Factors, Contrib Microbial Immunol, 10:48-114 (1989).
Di John et al., Effect of Priming with Carrier on Response to Conjugate Vaccine, Lancet 2(8677): 1415-1418 (1989).
Edwards, Group B streptococcal conjugate vaccine: a timely concept for which the time has come, Human Vaccine 4(6):444-448 (2008).
Evans, et al., Enhancement of antigen-specific immunity via the TLR4 ligands MPL™ adjuvant and Ribi.529, Expert Rev Vaccines 2(2): 219-229 (2003).
Fabbrini et al., A new flow-cytometry-based opsonophagocytosis assay for the rapid measurement of functional antibody levels against Group B Streptococcus, J Immunol Methods 378(1-2): 11-19 (2012).
Fukasawa, et al., Neisseria meningitidis serogroup C polysaccharide and serogroup B outer membrane vesicle conjugate as a bivalent meningococcus vaccine candidate, Vaccine, 17: 2951-2958 (1999).
Granoff et al., Effect of immunity to the carrier protein on antibody responses to Haemophilus influenzae type b conjugate vaccines, Vaccine11(Suppl 1): 46-51 (1993).
Granoff et al., Effect of Carrier Protein Priming on Antibody Responses to Haemophilus influenzae Type b conjugate Vaccines in Infants, JAMA 272: 1116-1121 (1994).
Guttormsen, et al., Rational chemical design of the carbohydrate in a glycoconjugate vaccine enhances IgM-to-IgG switching, PNAS 105(15) : 5903-5908 2008.
Heath and Feldman, Vaccination against Group B streptococcus, Expert Rev Vaccines, 4(2): 207-218 (2005).
Herzenberg, et al., Carrier-priming leads to hapten-specific suppression, Nature 285: 664-667 (1980).
Hoppenbrouwers et al., The *(ect of reconstitution of an Haemophilus infuenzae type b-tetanus toxoid conjugate (PRP-T) vaccine on the immune responses to a diphtheria±tetanus-whole cell pertussis (DTwP) vaccine: a five-year follow-up, Vaccine 17: 2588-2598 (1999).
Johri, et al., Group B Streptococcus: global incidence and vaccine development, Nature Reviews-Microbiology 4 (12): 932-942 (2006).
Kotloff, et al., Safety and immunogenicity of a tetravalent group B streptococcal polysaccharide vaccine in healthy adults, Vaccine 14(5): 446-450 (1996).
Lancaster, et al., Immunogenicity and physico-chemical characterisation of a candidate conjugate vaccine against group B streptococcus serotypes Ia, Ib and III, Vaccine 29: 3213-3221 (2011).
Lewis et al., Discovery and characterization of sialic acid O-acetylation in group B Streptococcus, PNAS 101(30): 11123-11128 (2004).
List of posters presented at Meningitis Research Foundation's conference "Meningitis and Septicaemia in Children and Adults"

(56) References Cited

OTHER PUBLICATIONS held Nov. 11-12, 2009, available at http://www.meningitis.org/conference#sthash.6RAnxqST.dpuf <http://www.meningitis.org/conference> (11 pages).

Madoff, et al., Maternal immunization of mice with group B streptococcal type III polysaccharide-beta C protein conjugate elicits protective antibody to multiple serotypes, J Clin Invest 94(1): 286-292 (1994).

Maione, et al., Identification of a universal Group B streptococcus vaccine by multiple genome screen, Science 309 (5731): 148-150 (2005).

Michon, et al., Group B Streptococcal Type II and III Conjugate Vaccines: Physicochemical Properties That Influence Immunogenicity, Clin Vaccine Immunol 13(8): 936-943 (2006).

Olander et al., Booster response to the tetanus and diphtheria toxoid carriers of 11-valent pneumococcal conjugate vaccine in adults and toddlers, Vaccine 20: 336-341 (2002).

Palazzi, et al., Use of Type V Group B Streptococcal Conjugate Vaccine in Adults 65-85 Years Old, J Infect Dis 190: 558-564 (2004).

Paoletti, et al., An Oligosaccharide-Tetanus Toxoid Conjugate Vaccine against Type III Group B Streptococcus, J Biol Chem 265(30): 18278-18283 (1990).

Paoletti, et al., Group B Streptococcus Type II Polysaccharide-Tetanus Toxoid Conjugate Vaccine, Infect Immun, 60(10): 4009-4014 (1992).

Paoletti, et al., Effects of Chain Length on the Immunogenicity in Rabbits of Group B Streptococcus Type III Oligosaccharide-Tetanus Toxoid Conjugates, J Clin Invest 89(1):203-209 (1992).

Paoletti, et al., Neonatal Mouse Protection against Infection with Multiple Group B Streptococcal (GBS) Serotypes by Maternal Immunization with a Tetravalent GBS Polysaccharide-Tetanus Toxoid Conjugate Vaccine, Infect & Immun 62(8): 3236-3243 (1994).

Paoletti, et al., Effects of Alum Adjuvant or a Booster Dose on Immunogenicity during Clinical Trials of Group B Streptococcal Type III Conjugate Vaccines, Infect & Immun 69(11): 6696-6701 (2001).

Paoletti, Lawrence C., Potency of clinical Group B streptococcal conjugate vaccines, Vaccine 19: 2118-2126 (2001).

Paoletti, et al., Vaccines to prevent neonatal GBS infection, Semin Neonatal 7(4):315-323 (2002).

Paoletti et al., Glycoconjugate vaccines to prevent group B streptococcal infections. Expert Opin Biol Ther 3 (6):975-984 (2003).

Pizza, et al., Identification of Vaccine Candidates Against Serogroup B Meningococcus by Whole-Genome Sequencing, Science 287:1816-1820 (2000).

Rappuoli et al., Towards third-generation whooping cough vaccines, Tibtech 9: 232-238 (1991).

* cited by examiner

A.

B.

IMMUNOGENIC COMPOSITIONS

RELATED APPLICATIONS

This application is the U.S. National Phase of International Application No. PCT/EP2013/070647, entitled "IMMUNOGENIC COMPOSITIONS," filed Oct. 3, 2013 and published in English, which claims the benefit of U.S. provisional application 61/744,880 filed Oct. 3, 2012 and of U.S. provisional application 61/799,123 filed Mar. 15, 2013, the complete contents of all of which are hereby incorporated herein by reference for all purposes.

TECHNICAL FIELD

This invention is in the field of combination vaccines, that is vaccines containing a mixture of immunogens from more than one pathogen, such that administration of the vaccine can simultaneously immunize a subject against more than one pathogen. In particular, the invention relates to combination vaccines containing conjugates of *Streptococcus agalactiae* capsular saccharides and carrier proteins.

BACKGROUND ART

Vaccines containing antigens from more than one pathogenic organism within a single dose are known as "multivalent" or "combination" vaccines. Various combination vaccines have been approved for human use in the EU and the USA, including trivalent vaccines for protecting against diphtheria, tetanus and pertussis ("DTP" vaccines) and trivalent vaccines for protecting against measles, mumps and rubella ("MMR" vaccines). Combination vaccines offer patients the advantage of receiving a reduced number of injections, which can lead to the clinical advantage of increased compliance (e.g. see chapter 29 of reference 1).

*Streptococcus agalactiae* (Group B *streptococcus*, GBS) is a haemolytic, encapsulated Gram positive microorganism that colonizes the anogenital tract of 25-30% healthy women. GBS causes neonatal infections in infants born to mothers carrying the bacteria and is a major cause of neonatal sepsis and meningitis. The pathogen is also increasingly recognized as an important cause of disease in adults, particularly those with underlying disease, and in the elderly.

Conjugate vaccines against *Streptococcus agalactiae* have been described in documents such as references 2 to 10. Conjugate vaccines for each of GBS serotypes Ia, Ib, II, III, and V have been shown to be safe and immunogenic in humans [11]. Reference 12 also discloses various GBS conjugate-containing vaccines.

It is an object of the invention to provide further and improved combination vaccines for protecting against *Streptococcus agalactiae* and one or more of *Corynebacterium diphtheriae, Clostridium tetani, Bordetella pertussis* and Poliovirus.

DISCLOSURE OF THE INVENTION

The invention is based on studies of combination vaccines that comprise GBS conjugates and one or more antigens selected from: a) cellular or acellular pertussis antigen, b) a tetanus toxoid, c) a diphtheria toxoid and d) an inactivated polio virus antigen. The inventors have found that these combination vaccines elicit specific antibody titers to the corresponding antigens with little or no immunological interference between the various antigens.

Thus, the invention provides an immunogenic composition comprising one or more GBS conjugates and one or more antigens selected from: a) cellular or acellular pertussis antigen, b) a tetanus toxoid, c) a diphtheria toxoid and d) an inactivated polio virus antigen, wherein each GBS conjugate is a group B *streptococcus* capsular saccharide conjugated to a carrier protein.

The invention also provides a method for raising an immune response in a patient, comprising the step of administering to the patient an immunogenic composition according to the invention.

The invention also provides a process for preparing the immunogenic composition according to the invention, comprising mixing a first component comprising one or more GBS conjugates and a second component comprising one or more antigens selected from: a) cellular or acellular pertussis antigen, b) a tetanus toxoid, c) a diphtheria toxoid and d) an inactivated polio virus antigen.

The invention also provides a kit for preparing the immunogenic composition of the invention, comprising a first component comprising one or more GBS conjugates; and a second component comprising one or more antigens selected from: a) cellular or acellular pertussis antigen, b) a tetanus toxoid, c) a diphtheria toxoid and d) an inactivated polio virus antigen; wherein the two components are in separate containers.

GBS Conjugate

Capsular Saccharide

The invention is based on the capsular saccharide of *Streptococcus agalactiae*. The capsular saccharide is covalently linked to the peptidoglycan backbone of GBS, and is distinct from the group B antigen, which is another saccharide that is attached to the peptidoglycan backbone.

The GBS capsular saccharides are chemically related, but are antigenically very different. All GBS capsular saccharides share the following trisaccharide core:

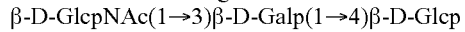

The various GBS serotypes differ by the way in which this core is modified. The difference between serotypes Ia and III, for instance, arises from the use of either the GlcNAc (Ia) or the Gal (III) in this core for linking consecutive trisaccharide cores. Serotypes Ia and Ib both have a [α-D-NeupNAc(2→3)β-D-Galp-(1→] disaccharide linked to the GlcNAc in the core, but the linkage is either 1→4 (Ia) or 1→3 (Ib).

GBS-related disease arises primarily from serotypes Ia, Ib, II, III, IV, V, VI, VII, and VIII, with over 85% being caused by five serotypes: Ia, Ib, III & V. The invention typically uses a saccharide from one or more of these four serotypes, particularly from one or more of serotypes: Ia, Ib & III. The capsular saccharides of each of these four serotypes include: (a) a terminal N-acetyl-neuraminic acid (NeuNAc) residue (commonly referred to as sialic acid), which in all cases is linked 2→3 to a galactose residue; and (b) a N-acetyl-glucosamine residue (GlcNAc) within the trisaccharide core. All four saccharides include galactose residues within the trisaccharide core, but serotypes Ia, Ib, II & III also contain additional galactose residues in each repeating unit.

In one embodiment, the immunogenic composition of the invention comprises one GBS conjugate. For example, the GBS conjugate may be a conjugate that is a capsular saccharide from GBS serotype Ia conjugated to a carrier protein. The GBS conjugate may be a conjugate that is a capsular saccharide from GBS serotype Ib conjugated to a carrier protein. The GBS conjugate may be a conjugate that is a capsular saccharide from GBS serotype III conjugated to a carrier protein. The GBS conjugate may be a conjugate that is a capsular saccharide from GBS serotype V conjugated to a carrier protein. The GBS conjugate may be a conjugate that is a capsular saccharide from GBS serotype II conjugated to a carrier protein.

The immunogenic compositions may comprise more than one GBS conjugate. Embodiments of the invention comprising two, three, four or five GBS conjugates are described below. In one embodiment, the first GBS conjugate is a capsular saccharide from GBS serotype Ia conjugated to a carrier protein, while the second GBS conjugate is a capsular saccharide from GBS serotype Ib conjugated to a carrier protein. In a second embodiment, the first GBS conjugate is a capsular saccharide from GBS serotype Ia conjugated to a carrier protein, while the second GBS conjugate is a capsular saccharide from GBS serotype III conjugated to a carrier protein. In a third embodiment, the first GBS conjugate is a capsular saccharide from GBS serotype Ia conjugated to a carrier protein, while the second GBS conjugate is a capsular saccharide from GBS serotype V conjugated to a carrier protein. In a fourth embodiment, the first GBS conjugate is a capsular saccharide from GBS serotype Ib conjugated to a carrier protein, while the second GBS conjugate is a capsular saccharide from GBS serotype III conjugated to a carrier protein. In a fifth embodiment, the first GBS conjugate is a capsular saccharide from GBS serotype Ib conjugated to a carrier protein, while the second GBS conjugate is a capsular saccharide from GBS serotype V conjugated to a carrier protein. In a sixth embodiment, the first GBS conjugate is a capsular saccharide from GBS serotype III conjugated to a carrier protein, while the second GBS conjugate is a capsular saccharide from GBS serotype V conjugated to a carrier protein. In a further embodiment, the first GBS conjugate is a capsular saccharide from GBS serotype Ia conjugated to a carrier protein, while the second GBS conjugate is a capsular saccharide from GBS serotype II conjugated to a carrier protein. In a further embodiment, the first GBS conjugate is a capsular saccharide from GBS serotype Ib conjugated to a carrier protein, while the second GBS conjugate is a capsular saccharide from GBS serotype II conjugated to a carrier protein. In a further embodiment, the first GBS conjugate is a capsular saccharide from GBS serotype III conjugated to a carrier protein, while the second GBS conjugate is a capsular saccharide from GBS serotype II conjugated to a carrier protein. In a further embodiment, the first GBS conjugate is a capsular saccharide from GBS serotype II conjugated to a carrier protein, while the second GBS conjugate is a capsular saccharide from GBS serotype V conjugated to a carrier protein.

Typically, the immunogenic composition of the invention comprises three GBS conjugates. Typically, the first GBS conjugate is a capsular saccharide from GBS serotype Ia conjugated to a carrier protein, while the second GBS conjugate is a capsular saccharide from GBS serotype Ib conjugated to a carrier protein and the third GBS conjugate is a capsular saccharide from GBS serotype III conjugated to a carrier protein. In an alternative embodiment, the first GBS conjugate is a capsular saccharide from GBS serotype Ia conjugated to a carrier protein, while the second GBS conjugate is a capsular saccharide from GBS serotype Ib conjugated to a carrier protein and the third GBS conjugate is a capsular saccharide from GBS serotype V conjugated to a carrier protein. In a further embodiment, the first GBS conjugate is a capsular saccharide from GBS serotype Ia conjugated to a carrier protein, while the second GBS conjugate is a capsular saccharide from GBS serotype III conjugated to a carrier protein and the third GBS conjugate is a capsular saccharide from GBS serotype V conjugated to a carrier protein. In another embodiment, the first GBS conjugate is a capsular saccharide from GBS serotype Ib conjugated to a carrier protein, while the second GBS conjugate is a capsular saccharide from GBS serotype III conjugated to a carrier protein and the third GBS conjugate is a capsular saccharide from GBS serotype V conjugated to a carrier protein. In a further embodiment, the first GBS conjugate is a capsular saccharide from GBS serotype Ia conjugated to a carrier protein, while the second GBS conjugate is a capsular saccharide from GBS serotype Ib conjugated to a carrier protein and the third GBS conjugate is a capsular saccharide from GBS serotype II conjugated to a carrier protein. In a further embodiment, the first GBS conjugate is a capsular saccharide from GBS serotype Ia conjugated to a carrier protein, while the second GBS conjugate is a capsular saccharide from GBS serotype II conjugated to a carrier protein and the third GBS conjugate is a capsular saccharide from GBS serotype III conjugated to a carrier protein. In another embodiment, the first GBS conjugate is a capsular saccharide from GBS serotype Ib conjugated to a carrier protein, while the second GBS conjugate is a capsular saccharide from GBS serotype II conjugated to a carrier protein and the third GBS conjugate is a capsular saccharide from GBS serotype III conjugated to a carrier protein. In another embodiment, the first GBS conjugate is a capsular saccharide from GBS serotype Ia conjugated to a carrier protein, while the second GBS conjugate is a capsular saccharide from GBS serotype II conjugated to a carrier protein and the third GBS conjugate is a capsular saccharide from GBS serotype V conjugated to a carrier protein. In another embodiment, the first GBS conjugate is a capsular saccharide from GBS serotype Ib conjugated to a carrier protein, while the second GBS conjugate is a capsular saccharide from GBS serotype II conjugated to a carrier protein and the third GBS conjugate is a capsular saccharide from GBS serotype V conjugated to a carrier protein. In another embodiment, the first GBS conjugate is a capsular saccharide from GBS serotype II conjugated to a carrier protein, while the second GBS conjugate is a capsular saccharide from GBS serotype III conjugated to a carrier protein and the third GBS conjugate is a capsular saccharide from GBS serotype V conjugated to a carrier protein.

In the same way, the immunogenic compositions may comprise four GBS conjugates. In one embodiment, the first GBS conjugate is a capsular saccharide from GBS serotype Ia conjugated to a carrier protein, while the second GBS conjugate is a capsular saccharide from GBS serotype Ib conjugated to a carrier protein, the third GBS conjugate is a capsular saccharide from GBS serotype III conjugated to a carrier protein and the fourth GBS conjugate is a capsular saccharide from GBS serotype V conjugated to a carrier protein. In one embodiment, the first GBS conjugate is a capsular saccharide from GBS serotype Ia conjugated to a carrier protein, while the second GBS conjugate is a capsular saccharide from GBS serotype Ib conjugated to a carrier protein, the third GBS conjugate is a capsular saccharide from GBS serotype II conjugated to a carrier protein and the fourth GBS conjugate is a capsular saccharide from GBS serotype III conjugated to a carrier protein. In one embodiment, the first GBS conjugate is a capsular saccharide from GBS serotype Ia conjugated to a carrier protein, while the second GBS conjugate is a capsular saccharide from GBS serotype Ib conjugated to a carrier protein, the third GBS conjugate is a capsular saccharide from GBS serotype II conjugated to a carrier protein and the fourth GBS conjugate is a capsular saccharide from GBS serotype V conjugated to a carrier protein. In one embodiment, the first GBS conjugate is a capsular saccharide from GBS serotype Ia conjugated to a carrier protein, while the second GBS conjugate is a capsular saccharide from GBS serotype II conjugated to a carrier protein, the third GBS conjugate is a capsular saccharide from GBS serotype III conjugated to a carrier protein and the fourth GBS conjugate is a capsular saccharide from GBS serotype V conjugated to a carrier protein. In one embodiment, the first GBS conjugate is a capsular saccharide from GBS serotype Ib conjugated to a carrier protein, while the second GBS conjugate is a capsular saccharide from GBS serotype II conjugated to a carrier protein, the third GBS conjugate is a capsular saccharide from GBS serotype III conjugated to a carrier protein and the fourth GBS conjugate is a capsular saccharide from GBS serotype V conjugated to a carrier protein.

In the same way, the immunogenic compositions may comprise five GBS conjugates. For example, the first GBS conjugate is a capsular saccharide from GBS serotype Ia conjugated to a carrier protein, while the second GBS conjugate is a capsular saccharide from GBS serotype Ib conjugated to a carrier protein, the third GBS conjugate is a capsular saccharide from GBS serotype III conjugated to a carrier protein, the fourth GBS conjugate is a capsular saccharide from GBS serotype V conjugated to a carrier protein and the fifth GBS conjugate is a capsular saccharide from GBS serotype II conjugated to a carrier protein.

Typically, the immunogenic compositions described above will not comprise any GBS conjugates other than those specifically mentioned, particularly GBS conjugates comprising capsular saccharides from GBS serotypes other than those specifically mentioned. However, in some embodiments, the compositions may comprise other GBS conjugates, including GBS conjugates comprising capsular saccharides from other GBS serotypes. For example, the compositions may comprise a GBS conjugate capsular saccharide from GBS serotype VI conjugated to a carrier protein. In another possibility, the compositions may comprise a GBS conjugate that is a capsular saccharide from GBS serotype VIII conjugated to a carrier protein.

Saccharides useful for the invention may be in their native form, or may have been modified. For example, the saccharide may be shorter than the native capsular saccharide, or may be chemically modified. In particular, the serotype V capsular saccharide used in the invention may be modified as described in refs. 13 and 14. For example, a serotype V capsular saccharide that has been substantially desialylated as described in refs. 13 and 14 is specifically envisaged for use in the present invention. Desialylated GBS serotype V capsular saccharide may be prepared by treating purified GBS serotype V capsular saccharide under mildly acidic conditions (e.g. 0.1M sulphuric acid at 80° C. for 60 minutes) or by treatment with neuraminidase, as described in reference 13. A preferred method for preparing desialylated GBS serotype V capsular saccharide is by treating the purified saccharide with 1M acetic acid at 81° C.+/−3 C.° for 2 h. Thus the saccharide used according to the invention may be a substantially full-length capsular polysaccharide, as found in nature, or it may be shorter than the natural length. Full-length polysaccharides may be depolymerised to give shorter fragments for use with the invention e.g. by hydrolysis in mild acid, by heating, by sizing chromatography, etc. Chain length has been reported to affect immunogenicity of GBS saccharides in rabbits [5]. In particular, the serotype II and/or III capsular saccharides used in the invention may be depolymerised as described in refs. 15 and 16. These documents describe the partial depolymerization of type II and type III capsular saccharides by mild deaminative cleavage to antigenic fragments with reducing-terminal 2,5-anhydro-D-mannose residues. Briefly, the capsular saccharide is dissolved in 0.5 N NaOH and heated at 70° C. for between about 1-4 h. The length of this incubation controls the degree of depolymerisation, which may be determined by standard methods (e.g. by HPLC as described in reference 15). The sample is chilled in an ice-water bath before glacial acetic acid is added to bring the pH to 4. The partially N-deacylated product is then deaminated by the addition of 5% (wt/vol) $NaNO_2$ with stirring at 4° C. for 2 h. The free aldehydes of the newly formed 2,5-anhydro-D-mannose residues may be used for conjugation to a carrier protein, as described in reference [12].

Depolymerisation of the serotype III capsular saccharide by endo-β-galactosidase has been reported [refs. 2 & 5-7], including using the depolymerised material to form conjugates with a tetanus toxoid carrier. Ozonolysis of capsular polysaccharides from GBS serotypes III and VIII has also been used for depolymerisation [17]. It is preferred to use saccharides with MW>30 kDa, and substantially full-length capsular polysaccharides can be used. For serotype Ia, it is preferred to use polysaccharides with a MW in the range of 150-400 kDa, particularly 300-350 kDa. Typically, a serotype Ia saccharide with MW about 330 kDa is used. For serotype Ib, it is preferred to use polysaccharides with a MW in the range of 150-400 kDa, particularly 250-300 kDa. Typically, a serotype Ib saccharide with MW about 280 kDa is used. For serotype III, it is preferred to use polysaccharides with a MW in the range of 50-200 kDa, particularly 100-150 kDa. Typically, a serotype III saccharide with MW about 140 kDa is used. For serotype V, it is also preferred to use polysaccharides with a MW in the range 50-200 kDa, particularly 150-200 kDa. Typically, a serotype V saccharide with MW about 180 kDa is used. These molecular masses can be measured by gel filtration relative to dextran standards, such as those available from Polymer Standard Service [18].

The saccharide may be chemically modified relative to the capsular saccharide as found in nature. For example, the saccharide may be de-O-acetylated (partially or fully), de-N-acetylated (partially or fully), N-propionated (partially or fully), etc. De-acetylation may occur before, during or after conjugation, but preferably occurs before conjugation. Depending on the particular saccharide, de-acetylation may or may not affect immunogenicity. The relevance of O-acetylation on GBS saccharides in various serotypes is discussed in reference 19, and in some embodiments O-acetylation of sialic acid residues at positions 7, 8 and/or 9 is retained before, during and after conjugation e.g. by protection/de-protection, by re-acetylation, etc. However, typically the GBS saccharide used in the present invention has substantially no O-acetylation of sialic acid residues at positions 7, 8 and/or 9. In particular, when the GBS saccharide has been purified by base extraction as described in reference [12], then O-acetylation is typically lost (ref. 19). The effect of de-acetylation etc. can be assessed by routine assays.

Capsular saccharides can be purified by known techniques, as described in the references herein such as refs. 3 and 20. A typical process involves base extraction, centrifugation, filtration, RNase/DNase treatment, protease treatment, concentration, size exclusion chromatography, ultrafiltration, anion exchange chromatography, and further ultrafiltration. Treatment of GBS cells with the enzyme mutanolysin, which cleaves the bacterial cell wall to free the cell wall components, is also useful.

As an alternative, the purification process described in reference 21 can be used. This involves base extraction, ethanol/$CaCl_2$ treatment, CTAB precipitation, and re-solubilisation. A further alternative process is described in reference 22.

The invention is not limited to saccharides purified from natural sources, however, and the saccharides may be obtained by other methods, such as total or partial synthesis.

The immunogenic compositions described above may comprise any suitable amount of the capsular saccharide(s) per unit dose. Within each dose, the quantity of an individual saccharide antigen will generally be between 0.1-50 μg (measured as mass of saccharide), particularly between 1-50 μg or 0.5-25 μg, more particularly 2.5-7.5 μg, e.g. about 1 μg, about 2.5 μg, about 5 μg, about 10 μg, about 15 μg, about 20 μg or about 25 μg. Within each dose, the total quantity of GBS capsular saccharides will generally be ≤70 μg (measured as mass of saccharide), e.g. ≤60 μg. In particular, the total quantity may be ≤40 μg (e.g. ≤30 μg) or ≤20 μg (e.g. ≤15 μg). These total quantities are particularly effective when the immunogenic composition comprises: i) a conjugate that is a capsular saccharide from GBS serotype Ia conjugated to a carrier protein; ii) a conjugate that is a capsular saccharide from GBS serotype Ib conjugated to a carrier protein; and iii) a conjugate that is a capsular saccharide from GBS serotype III conjugated to a carrier protein. It may be advantageous to minimise the total quantity of capsular saccharide(s) per unit dose in order to reduce potential toxicity. Accordingly, the invention typically uses a total quantity of ≤20 μg, e.g. ≤15 μg, ≤7.5 μg or ≤1.5 μg.

It may be possible to further minimise the amount of capsular saccharide(s) per unit dose. In particular, suitable amounts of the capsular saccharide(s) may be from 0.1 to 5 μg per unit dose. Typically, each GBS capsular saccharide may therefore be present at an amount from 0.1 to 5 μg, e.g. 0.5, 2.5 or 5 μg, per unit dose. For example, each GBS capsular saccharide may be present at an amount from 0.5 to 5 μg, 1 to 4 μg, 2 to 3 μg, or about 2.5 μg per unit dose. These amounts are particularly effective when the immunogenic composition comprises i) a conjugate that is a capsular saccharide from GBS serotype Ia conjugated to a carrier protein; ii) a conjugate that is a capsular saccharide from GBS serotype Ib conjugated to a carrier protein; and iii) a conjugate that is a capsular saccharide from GBS serotype III conjugated to a carrier protein.

In the embodiments described above wherein the immunogenic composition comprises more than one GBS conjugate, the ratio of the mass of a given capsular saccharide to the mass of the other capsular saccharide(s) may vary. For example, where the immunogenic composition comprises GBS serotype Ia, Ib and III capsular saccharides, the ratio of the masses of the GBS serotype Ia, Ib and III capsular saccharides is 1:1:1.

Conjugation

The invention uses GBS conjugates that are capsular saccharides from GBS serotypes Ia, Ib, II, III or V conjugated to a carrier protein. As used herein, the term "conjugate" refers to a compound formed by covalent binding of two parts to form a single structure, wherein the first part is an antigen, particularly a polysaccharide, and the second part is an immunogenic carrier such as a carrier protein. The binding can be made by a covalent chemical bond between the molecules or by use of a linking group, nonexclusively including diaminoalkanes and one or more amino acids, one of which provides a free sulfhydryl, carboxyl, amino or other group for conjugation to the carrier. For the purposes of the invention, generally the term 'conjugate' is refers to a bacterial antigen, particularly a bacterial saccharide or polysaccharide, linked covalently to a carrier protein. In general, covalent conjugation of saccharides to carriers enhances the immunogenicity of saccharides as it converts them from T-independent antigens to T-dependent antigens, thus allowing priming for immunological memory. Conjugation is particularly useful for paediatric vaccines [e.g. ref. 23] and is a well known technique [e.g. reviewed in refs. 24 to 32]. Thus the processes of the invention may include the further step of conjugating the purified saccharide to a carrier molecule.

Conjugation of GBS saccharides has been widely reported e.g. see references 2 to 103567. typical prior art process for GBS saccharide conjugation typically involves reductive amination of a purified saccharide to a carrier protein such as tetanus toxoid (TT) or CRM197 [3]. The reductive amination involves an amine group on the side chain of an amino acid in the carrier and an aldehyde group in the saccharide. As GBS capsular saccharides do not include an aldehyde group in their natural form then this is typically generated before conjugation by oxidation (e.g. periodate oxidation) of a portion (e.g. between 5 and 40%, particularly between 10 and 30%, preferably about 20%) of the saccharide's sialic acid residues [3,33]. Conjugate vaccines prepared in this manner have been shown to be safe and immunogenic in humans for each of GBS serotypes Ia, Ib, II, III, and V [11]. Typically, all of the conjugates in the immunogenic compositions of the present invention have been prepared in this manner. However, when the invention uses a serotype V capsular saccharide that is desialylated, then an aldehyde group may be generated in this saccharide before conjugation by oxidation (e.g. periodate oxidation) of a portion (e.g. between 5 and 40%, particularly between 10 and 30%, preferably about 20%) of the saccharide's galactose residues [2,33]. An alternative conjugation process involves the use of —$NH_2$ groups in the saccharide (either from de-N-acetylation, or after introduction of amines) in conjunction with bifunctional linkers, as described in ref. 34. In some embodiments, one or more of the conjugates in the immunogenic compositions of the present invention have been prepared in this manner. A further alternative process is described in refs. 15 and 16. In this process, the free aldehydes groups of terminal 2,5-anhydro-D-mannose residues from depolymerization of type II or type III capsular saccharides by mild deaminative cleavage are used for conjugation by reductive amination. In some embodiments, one or more of the conjugates in the immunogenic compositions of the present invention have been prepared in this manner. Conjugates may be prepared by separate processes and combined into a single dosage formulation.

Carrier Protein

The invention involves the use of carrier proteins. Although polysaccharides are immunogenic on their own, conjugation of polysaccharides to carrier proteins can improve or enhance immunogenicity. Therefore, as used herein, the term "carrier" refers to an immunogenic substance which, when conjugated to an antigen (such as a polysaccharide) and administered to an animal, will induce or enhance an immune response in the animal, particularly a protective immune response, and elicit the production of antibodies that bind specifically to the antigen, for example, the above described polysaccharides. Useful carrier proteins include bacterial toxins or toxoids, such as diphtheria toxoid or tetanus toxoid. Fragments of toxins or toxoids can also be used e.g. fragment C of tetanus toxoid [35].

The CRM197 mutant of diphtheria toxin [36-38] is a particularly useful carrier for use in the present invention. Diphtheria is an acute, often fatal bacterial disease caused by *Corynebacterium diphtheria* and clinical manifestations of the disease are due mainly to the presence of circulating diphtheria toxin. Active immunization programs against diphtheria have generally been based on preparations containing a diphtheria toxoid produced by formaldehyde detoxification of diphtheria toxin (see below). The cross-reacting material (CRM197) is a genetically detoxified preparation of diphtheria toxin. CRM197 differs from diphtheria toxin (DT) in only a single amino acid and is therefore highly cross-reactive with DT (CRM=cross reactive material). This mutant of diphtheria toxin does not require detoxification with formaldehyde, and homogeneous preparations of purified antigen can be readily obtained, for example, from cultures of *Corynebacterium diphtheria* strain C7 (beta197) grown in casamino acids and yeast extract medium. Alternatively CRM197 may be prepared recombinantly in accordance with U.S. Pat. No. 5,614,382. CRM197 is licensed for human use as a carrier protein for several capsular polysaccharide antigens and is a potential alternative to conventional diphtheria toxoid prepared by formaldehyde treatment. As described below, the use of CRM197 as a carrier may be advantageous since this carrier can also elicit the production of antibodies against *Corynebacterium diphtheria*.

Other suitable carrier proteins include the *N. meningitidis* outer membrane protein [39], synthetic peptides [40,41], heat shock proteins [42,43], pertussis proteins [44,45], cytokines [46], lymphokines [46], hormones [46], growth factors [46], human serum albumin (preferably recombinant), artificial proteins comprising multiple human CD4+ T cell epitopes from various pathogen-derived antigens [47] such as N19 [48], protein D from *H. influenzae* [49,50], pneumococcal surface protein PspA [51], pneumolysin [52], iron-uptake proteins [53], toxin A or B from *C. difficile* [54], recombinant *Pseudomonas aeruginosa* exoprotein A (rEPA) [55], a GBS protein (particularly GBS67) [56], etc.

Attachment to the carrier is preferably via a —NH$_2$ group e.g. in the side chain of a lysine residue in a carrier protein, or of an arginine residue, or at the N-terminus. Attachment may also be via a —SH group e.g. in the side chain of a cysteine residue.

It is possible to use more than one carrier protein e.g. to reduce the risk of carrier suppression. Thus different carrier proteins can be used for different GBS serotypes e.g. serotype Ia saccharides might be conjugated to CRM197 while serotype Ib saccharides might be conjugated to tetanus toxoid. It is also possible to use more than one carrier protein for a particular saccharide antigen e.g. serotype III saccharides might be in two groups, with some conjugated to CRM197 and others conjugated to tetanus toxoid. In general, however, it is typical to use the same carrier protein for all saccharides.

A single carrier protein might carry more than one saccharide antigen [57,58]. For example, a single carrier protein might have conjugated to it saccharides from serotypes Ia and Ib. To achieve this goal, different saccharides can be mixed prior to the conjugation reaction. In general, however, it is preferred to have separate conjugates for each serogroup, with the different saccharides being mixed after conjugation. The separate conjugates may be based on the same carrier.

GBS conjugates with a saccharide:protein ratio (w/w) of between 1:5 (i.e. excess protein) and 5:1 (i.e. excess saccharide) are typically used, in particular ratios between 1:5 and 2:1. When the invention uses a GBS conjugate that is a capsular saccharide from GBS serotype Ia conjugated to a carrier protein, then the saccharide:protein ratio (w/w) is typically between about 1:1 to 1:2, particularly about 1:1.3. Similarly, when the invention uses a conjugate that is a capsular saccharide from GBS serotype Ib conjugated to a carrier protein, then the ratio is typically between about 1:1 to 1:2, particularly about 1:1.3. When the invention uses a conjugate that is a capsular saccharide from GBS serotype III conjugated to a carrier protein, then the saccharide:protein ratio (w/w) is typically between about 3:1 to 1:1, particularly about 2:1. However, GBS serotype III conjugated to a carrier protein with a saccharide:protein ratio (w/w) of about 1:1 to 1:5, particularly about 1:3.3, may also be used. When the invention uses a conjugate that is a capsular saccharide from GBS serotype II conjugated to a carrier protein, then the ratio is typically between about 2:1 to 1:1 Finally, when the invention uses a conjugate that is a capsular saccharide from GBS serotype V conjugated to a carrier protein, then the ratio is typically between about 2:1 to 1:1, particularly about 1.1:1. Thus a weight excess of saccharide is typical, particularly with longer saccharide chains.

Compositions may include a small amount of free carrier [59]. When a given carrier protein is present in both free and conjugated form in a composition of the invention, the unconjugated form is typically no more than 5% of the total amount of the carrier protein in the composition as a whole, for example, present at less than 2% by weight.

After conjugation, free and conjugated saccharides can be separated. There are many suitable methods, including hydrophobic chromatography, tangential ultrafiltration, diafiltration etc. [see also refs. 60 & 61, etc.]. A preferred method is described in reference 62.

Where the composition of the invention includes a depolymerised oligosaccharide, it is preferred that depolymerisation precedes conjugation.

One or More Antigens

An "antigen" is a compound, composition, or substance which stimulates an immune response in the body, particularly a protective immune response by stimulating the production of antibodies and/or a T cell response. Whilst the above described bacterial polysaccharide conjugates are antigens, as used herein generally the term 'antigen' will be used to refer to diphtheria toxoid(s), tetanus toxoid(s), pertussis toxoid(s), cellular pertussis antigen(s), acellular pertussis antigen(s) and poliovirus antigen(s), including inactivated poliovirus antigens described below. Thus, the term will be used to distinguish the conjugated component(s) which primarily provide protection against *Streptococcus agalactiae* from the component(s) providing protection against *Corynebacterium diphtheriae, Clostridium tetani, Bordetella pertussis* and/or Poliovirus. The term "one or more" as used herein, refers to one, two, three, four, five, six, seven, eight, nine, ten, or more.

Diphtheria Toxoid

Diphtheria is caused by *Corynebacterium diphtheriae*, a Gram-positive non-sporing aerobic bacterium. This organism expresses a prophage-encoded ADP-ribosylating exotoxin ('diphtheria toxin'), which can be treated (e.g. using formaldehyde) to give a toxoid that is no longer toxic but that remains antigenic and is able to stimulate the production of specific anti-toxin antibodies after injection. Diphtheria toxoids are disclosed in more detail in chapter 13 of reference 63. Preferred diphtheria toxoids are those prepared by formaldehyde treatment. The diphtheria toxoid can be obtained by growing *C. diphtheriae* in growth medium (e.g. Fenton medium, or Linggoud & Fenton medium), which may be supplemented with bovine extract, followed by formaldehyde treatment, ultrafiltration and precipitation. The toxoided material may then be treated by a process comprising sterile filtration and/or dialysis.

Quantities of diphtheria toxoid can be expressed in international units (IU). For example, the NIBSC [64] supplies the 'Diphtheria Toxoid Adsorbed Third International Standard 1999' [65,66], which contains 160 IU per ampoule. As an alternative to the IU system, the 'Lf' unit ("flocculating units", the "limes flocculating dose", or the "limit of flocculation") is defined as the amount of toxoid which, when mixed with one International Unit of antitoxin, produces an optimally flocculating mixture [67]. For example, the NIBSC supplies 'Diphtheria Toxoid, Plain' [68], which contains 300 Lf per ampoule, 'The 1st International Reference Reagent For Diphtheria Toxoid For Flocculation Test' [69] which contains 900 Lf per ampoule. The conversion between IU and Lf systems depends on the particular toxoid preparation.

Where bovine materials are used in the culture of *C. diphtheriae*, they should be obtained from sources that are free from bovine spongiform encephalopathy (BSE) or from other transmissible spongiform encephalopathies (TSEs).

The diphtheria toxoid in the immunogenic compositions of the invention is typically present in an amount that is capable of eliciting an immune response when administered. Ideally, diphtheria toxoid can elicit a protective immune response. The amount of diphtheria toxoid in the immunogenic compositions of the invention is typically 1-50 Lf/dose. Booster vaccines for adolescents and adults typically contain between 4 Lf/ml and 8 Lf/ml of diphtheria toxoid, e.g. 2.5 Lf, preferably 4 Lf, per 0.5 ml dose. Paediatric vaccines typically contain between 20 and 50 Lf/ml of diphtheria toxoid, e.g. 10 Lf or 25 Lf per 0.5 ml dose.

For paediatric combination vaccines, the ratio of diphtheria toxoid to tetanus toxoid is typically greater than 1 (i.e. paediatric vaccines usually have an excess of diphtheria toxoid) and generally between 2:1 and 3:1 (measured in Lf units), e.g. 2.5:1. In contrast, for booster vaccine that are administered to adolescents or adults (who usually have received at least one paediatric combination vaccine comprising diphtheria toxoid and tetanus toxoid), the ratio of diphtheria toxoid to tetanus toxoid is typically greater than 1 (i.e. booster vaccines usually have an excess of tetanus toxoid) and generally between 1.5:1 and 2.5:1, e.g. 2:1. The diphtheria toxoid is typically unconjugated.

The skilled person will understand that the "diphtheria component", in other words that part of the immunogenic composition which is used for eliciting an immune response which provides protection against *Corynebacterium diphtheria*, may be provided in the form of CRM197, diphtheria toxoid or a combination of these.

In some embodiments when CRM197 is present as a carrier protein, i.e. as part of a conjugate, the amount of unconjugated ("free") diphtheria toxoid in compositions of the invention may be reduced. In other embodiments when CRM197 is present as a carrier protein, i.e. as part of a conjugate, diphtheria toxoid is not present and may be absent from the compositions of the invention but the immunogenic composition may still be able to elicit an immune response that provides protection against *C. diphtheria*. Therefore, when immunogenic compositions comprise both unconjugated and conjugated diphtheria toxoid and/or CRM197, the total amount of diphtheria toxoid/CRM197 may be equivalent to 1-50 Lf/dose, at a concentration of between 4 Lf/ml and 8 Lf/ml, for example 2.5 Lf per 0.5 ml dose or 4 Lf per 0.5 ml dose, at a concentration of between 20 and 50 Lf/ml, for example 10 Lf per 0.5 ml dose or 25 Lf per 0.5 ml dose. In particular embodiments where diphtheria toxoid is absent, the amount of CRM197 present may be equivalent to 1-50 Lf/dose, at a concentration of between 4 Lf/ml and 8 Lf/ml, for example 2.5 Lf per 0.5 ml dose or 4 Lf per 0.5 ml dose, at a concentration of between 20 and 50 Lf/ml, for example 10 Lf per 0.5 ml dose or 25 Lf per 0.5 ml dose.

The diphtheria toxoid may be adsorbed onto an aluminium hydroxide adjuvant.

Typically, the immunogenic composition comprising diphtheria toxoid antigen is substantially free from any mercurial preservatives.

Tetanus Toxoid

Tetanus is caused by *Clostridium tetani*, a Gram-positive, spore-forming *bacillus*. This organism expresses an endopeptidase ('tetanus toxin'), which can be treated to give a toxoid that is no longer toxic but that remains antigenic and is able to stimulate the production of specific anti-toxin antibodies after injection. Tetanus toxoids are disclosed in more detail in chapter 27 of reference 1. Preferred tetanus toxoids are those prepared by formaldehyde treatment. The tetanus toxoid can be obtained by growing *C. tetani* in growth medium (e.g. a Latham medium derived from bovine casein), followed by formaldehyde treatment, ultrafiltration and precipitation. The material may then be treated by a process comprising sterile filtration and/or dialysis.

Quantities of tetanus toxoid can be expressed in international units (IU). For example, the NIBSC [70] supplies the 'Tetanus Toxoid Adsorbed Third International Standard 2000' [71,72], which contains 469 IU per ampoule. As an alternative to the IU system, the 'Lf' unit is defined as the amount of toxoid which, when mixed with one International Unit of antitoxin, produces an optimally flocculating mixture [73]. For example, the NIBSC supplies 'The 1st International Reference Reagent for Tetanus Toxoid For Flocculation Test' [74] which contains 1000 LF per ampoule. The conversion between IU and Lf systems depends on the particular toxoid preparation.

Where bovine materials are used in the culture of *C. tetani*, they should be obtained from sources that are free from bovine spongiform encephalopathy (BSE) or from other transmissible spongiform encephalopathies (TSEs).

The tetanus toxoid in the immunogenic compositions of the invention is typically present in an amount that is capable of eliciting an immune response when administered. Ideally, tetanus toxoid can elicit a protective immune response. The amount of tetanus toxoid in immunogenic compositions of the invention is typically 1-20 Lf per dose. Booster vaccines for adolescents and adults typically contain 5 Lf of tetanus toxoid per 0.5 ml dose. Paediatric vaccines typically contain between 5 and 10 Lf of tetanus toxoid per 0.5 ml dose.

The tetanus toxoid is typically unconjugated. However, it will be apparent to one skilled in the art that in some embodiments, tetanus toxoid may be present in both free (unconjugated) and conjugated form or primarily in conjugated form, that is more than 80, 85, 90, 91, 92, 93, 94, 95, 96, 97, 98, 99% of the tetanus toxoid is present in conjugated form. Thus, the amount of tetanus toxoid in immunogenic compositions of the invention may refer to unconjugated tetanus toxoid alone, conjugated tetanus toxoid alone or the sum of unconjugated and conjugated tetanus toxoid. In particular embodiments, tetanus toxoid is not conjugated to a GBS capsular polysaccharide. In particular embodiments, tetanus toxoid is conjugated to a *Haemophilus* b antigen. In particular embodiments, tetanus toxoid may be present as part of a GBS capsular polysaccharide conjugate and as a part of a conjugate to a non-GBS antigen. For the purposes of clarity, in some instances tetanus toxoid in conjugated form may be referred to using the nomenclature "-TT".

The tetanus toxoid may be adsorbed onto an aluminium hydroxide adjuvant, but this is not necessary (e.g. adsorption of between 0-10% of the total tetanus toxoid can be used).

Typically, the immunogenic composition comprising tetanus toxoid is substantially free from any mercurial preservatives.

Pertussis Toxoid

*Bordetella pertussis* is a Gram-negative non-sporing aerobic bacterium that causes whooping cough. As described in more detail in chapter 21 of reference 1, vaccines against *B. pertussis* have been available for many years, and fall into two categories: cellular (wP) and acellular (aP). Cellular vaccines comprise whole *B. pertussis* cells which have been killed and deactivated (e.g. by treatment with formalin and/or heat), whereas acellular vaccines comprise specific purified *B. pertussis* antigens, either purified from the native bacterium or purified after expression in a recombinant host.

Cellular Pertussis Antigens

The invention may use cellular pertussis antigens, in the form of inactivated *B. pertussis* cells. Preparation of cellular pertussis antigens is well documented (e.g. see chapter 21 of reference 1) e.g. it may be obtained by heat inactivation of phase I culture of *B. pertussis*.

Quantities of wP antigens can be expressed in international units (IU). For example, the NIBSC supplies the 'Third International Standard For Pertussis Vaccine' [75], which contains 46 IU per ampoule. Each ampoule contains the freeze-dried residue of 2.0 ml aliquots of an aqueous solution which contained 10 liters of bacterial suspension (equivalent to 180 opacity units in terms of the U.S. Opacity Standard) diluted with eight liters of M/15 Sorensen's buffer pH 7.0. As an alternative to the IU system, the 'OU' unit ("opacity units") is also used (e.g. 4 OU may be about 1 IU).

The cellular pertussis antigen in the immunogenic compositions of the invention is typically present in an amount that is capable of eliciting an immune response when administered. Ideally, the cellular pertussis antigen can elicit a protective immune response. The amount of wP antigen in immunogenic compositions of the invention is typically at least 4 IU/dose.

The cellular pertussis antigen may be adsorbed onto or mixed with an aluminium phosphate adjuvant.

Acellular Pertussis Antigen

The invention may use more than one acellular pertussis (aP) antigen in a single vaccine e.g. two or three of the following well-known and well-characterized *B. pertussis* antigens: (1) detoxified pertussis toxin (pertussis toxoid, or 'PT'); (2) filamentous hemagglutinin ('FHA'); (3) pertactin (also known as the '69 kiloDalton outer membrane protein'). It is most preferred that all three of these antigens should be used. These three antigens are preferably prepared by isolation from *B. pertussis* culture grown in modified Stainer-Scholte liquid medium. PT and FHA can be isolated from the fermentation broth (e.g. by adsorption on hydroxyapatite gel), whereas pertactin can be extracted from the cells by heat treatment and flocculation (e.g. using barium chloride). The antigens can be purified in successive chromatographic and/or precipitation steps. PT and FHA can be purified by hydrophobic chromatography, affinity chromatography and size exclusion chromatography. Pertactin can be purified by ion exchange chromatography, hydrophobic chromatography and size exclusion chromatography.

FHA and pertactin may be treated with formaldehyde prior to use according to the invention. PT is preferably detoxified by treatment with formaldehyde and/or glutaraldehyde. As an alternative to this chemical detoxification procedure the PT may be a mutant PT in which enzymatic activity has been reduced by mutagenesis [76], but detoxification by chemical treatment is preferred.

Further acellular pertussis antigens that can be used include fimbriae (e.g. agglutinogens 2 and 3).

The aP antigen(s) may be used in an unadsorbed state, but they are preferably adsorbed onto one or more aluminium salt adjuvant(s) before being used. The aP antigens are preferably adsorbed onto an aluminium hydroxide adjuvant.

Typically, the immunogenic composition comprising aP antigens are substantially free from mercurial preservatives (e.g. thimerosal).

The acellular pertussis antigen is typically present in the immunogenic compositions of the invention in an amount that is capable of eliciting an immune response when administered. Ideally, the acellular pertussis antigen can elicit a protective immune response. Quantities of acellular pertussis antigens are typically expressed in micrograms. The concentration of PT in a vaccine is usually between 5 and 50 µg/ml. Typical PT concentrations are 5 µg/ml, 16 µg/ml, 20 µg/ml or 50 µg/ml. The concentration of FHA in a vaccine is usually between 10 and 50 µg/ml. Typical FHA concentrations are 10 µg/ml, 16 µg/ml or 50 µg/ml. The concentration of pertactin in a vaccine is usually between 5 and 16 µg/ml. Typical pertactin concentrations are 5 µg/ml, 6 µg/ml or 16 µg/ml. For example, a booster vaccine for adolescents and adults typically contains 2.5 to 8 µg PT, between 4 and 8 µg FHA and between 2.5 and 8 µg pertactin per 0.5 ml dose. Typically, a booster vaccine comprises 4 µg PT, 4 µg FHA and 8 µg pertactin, more preferably 5 µg PT, 2.5 µg FHA and 2.5 µg pertactin, per 0.5 ml dose. A paediatric vaccine usually comprises 7 µg PT, 10 µg FHA and 10 µg pertactin, per 0.5 ml dose.

Where the aqueous component includes each of PT, FHA and pertactin, their weight ratios can vary, but may be e.g. about 16:16:5, about 5:10:6, about 20:20:3, about 25:25:8, or about 10:5:3 (PT:FHA:PRN).

Inactivated Poliovirus Antigens

Poliomyelitis can be caused by one of three types of poliovirus. The three types are similar and cause identical symptoms, but they are antigenically very different and infection by one type does not protect against infection by others. As explained in chapter 24 of reference 1, it is therefore preferred to use three poliovirus antigens in the immunogenic compositions of the invention—poliovirus Type 1 (e.g. Mahoney strain), poliovirus Type 2 (e.g. MEF-1 strain), and poliovirus Type 3 (e.g. Saukett strain).

Immunogenic compositions of the invention may include an inactivated poliovirus antigen.

Polioviruses may be grown in cell culture. A preferred culture uses a Vero cell line, which is a continuous cell line derived from monkey kidney. Vero cells can conveniently be cultured microcarriers. Culture of the Vero cells before and during viral infection may involve the use of bovine-derived material, such as calf serum, and of lactalbumin hydrolysate (e.g. obtained by enzymatic degradation of lactalbumin). Such bovine-derived material should be obtained from sources which are free from BSE or other TSEs. Preferably, polioviruses are grown in cells cultured in medium free of animal-derived components. After growth, virions may be purified using techniques such as ultrafiltration, diafiltration, and chromatography. Prior to administration to patients, polioviruses must be inactivated, and this can be achieved by treatment with formaldehyde before the viruses are used in the immunogenic compositions of the invention.

The three polioviruses are preferably grown, purified and inactivated individually, and are then combined to give a mixture for use in the invention.

The combined polioviruses may be adsorbed onto aluminium adjuvants.

Typically, the immunogenic composition comprising IPV antigens is substantially free from mercurial preservatives (e.g. thimerosal).

Quantities of IPV antigens are typically expressed in the 'DU' unit (the "D-antigen unit" [77]). The IPV antigens in the immunogenic compositions of the invention are typically present in an amount that is capable of eliciting an immune response when administered. Ideally, the IPV antigens can elicit a protective immune response.

Combination vaccine usually comprise between 1-100 DU per poliovirus type per dose e.g., about 40 DU of type 1 poliovirus, about 8 DU of type 2 poliovirus, and about 32 DU of type 3 poliovirus, but it is possible to use lower doses than these [78,79] e.g. 10-20 DU for type 1, 2-4 DU for type 2, and 8-20 DU for type 3. Preferably, a combination vaccine of the invention includes a 'low dose' of a poliovirus. For a Type 1 poliovirus this means that the concentration of the virus in the composition is <20 DU/ml e.g. <18, <16, <14, <12, <10, etc. For a Type 2 poliovirus this means that the concentration of the virus in the composition is <4 DU/ml e.g. <3, <2, <1, <0.5, etc. For a Type 3 poliovirus this means that the concentration of the virus in the composition is <16 DU/ml e.g. <14, <12, <10, <8, <6, etc. Where all three of Types 1, 2 and 3 poliovirus are present the three antigens can be present at a DU ratio of 5:1:4 respectively, or at any other suitable ratio e.g. a ratio of 15:32:45 when using Sabin strains [80]. A low dose of antigen from Sabin strains is particularly useful, with <10 DU type 1, <20 DU type 2, and <30 DU type 3 (per unit dose, typically 0.5 ml).

Where an IPV component is used, and the polioviruses were grown on Vero cells, a vaccine composition preferably contains less than 10 ng/ml, preferably <1 ng/ml e.g. <500 pg/ml or <50 pg/ml of Vero cell DNA e.g. less than 10 ng/ml of Vero cell DNA that is >50 base pairs long.

Specific Immunogenic Compositions of the Invention

Specifically envisaged immunogenic compositions of the invention comprise:

- (i) a conjugate that is a capsular saccharide from GBS serotype Ia conjugated to a carrier protein, (ii) a conjugate that is a capsular saccharide from GBS serotype Ib conjugated to a carrier protein, (iii) a conjugate that is a capsular saccharide from GBS serotype III conjugated to a carrier protein and (iv) a diphtheria toxoid.
- (i) a conjugate that is a capsular saccharide from GBS serotype Ia conjugated to a carrier protein, (ii) a conjugate that is a capsular saccharide from GBS serotype Ib conjugated to a carrier protein, (iii) a conjugate that is a capsular saccharide from GBS serotype III conjugated to a carrier protein and (iv) a tetanus toxoid.
- (i) a conjugate that is a capsular saccharide from GBS serotype Ia conjugated to a carrier protein, (ii) a conjugate that is a capsular saccharide from GBS serotype Ib conjugated to a carrier protein, (iii) conjugate that is a capsular saccharide from GBS serotype III conjugated to a carrier protein, (iv) a diphtheria toxoid and (v) a tetanus toxoid.
- (i) a conjugate that is a capsular saccharide from GBS serotype Ia conjugated to a carrier protein, (ii) a conjugate that is a capsular saccharide from GBS serotype Ib conjugated to a carrier protein, (iii) a conjugate that is a capsular saccharide from GBS serotype III conjugated to a carrier protein, (iv) a diphtheria toxoid, (v) a tetanus toxoid, (vi) a cellular pertussis antigen.
- (i) a conjugate that is a capsular saccharide from GBS serotype Ia conjugated to a carrier protein, (ii) a conjugate that is a capsular saccharide from GBS serotype Ib conjugated to a carrier protein, (iii) a conjugate that is a capsular saccharide from GBS serotype III conjugated to a carrier protein, (iv) a diphtheria toxoid, (v) a tetanus toxoid, (vi) acellular pertussis antigen.
- (i) a conjugate that is a capsular saccharide from GBS serotype Ia conjugated to a carrier protein, (ii) a conjugate that is a capsular saccharide from GBS serotype Ib conjugated to a carrier protein, (iii) a conjugate that is a capsular saccharide from GBS serotype III conjugated to a carrier protein, (iv) a diphtheria toxoid, (v) a tetanus toxoid, (vi) detoxified pertussis toxin, (vii) filamentous hemagglutinin and (viii) pertactin.
- (i) a conjugate that is a capsular saccharide from GBS serotype Ia conjugated to a carrier protein, (ii) a conjugate that is a capsular saccharide from GBS serotype Ib conjugated to a carrier protein, (iii) a conjugate that is a capsular saccharide from GBS serotype III conjugated to a carrier protein, (iv) a diphtheria toxoid, (v) a tetanus toxoid, (vi) acellular pertussis antigen and (vii) an inactivated polio virus antigen.
- (i) a conjugate that is a capsular saccharide from GBS serotype Ia conjugated to a carrier protein, (ii) a conjugate that is a capsular saccharide from GBS serotype Ib conjugated to a carrier protein, (iii) a conjugate that is a capsular saccharide from GBS serotype III conjugated to a carrier protein, (iv) a diphtheria toxoid, (v) a tetanus toxoid, (vi) detoxified pertussis toxin, (vii) filamentous hemagglutinin, (viii) pertactin and (ix) an inactivated polio virus antigen.
- (i) a conjugate that is a capsular saccharide from GBS serotype Ia conjugated to a carrier protein, (ii) a conjugate that is a capsular saccharide from GBS serotype Ib conjugated to a carrier protein, (iii) a conjugate that is a capsular saccharide from GBS serotype III conjugated to a carrier protein, (iv) a diphtheria toxoid, (v) a tetanus toxoid, (vi) detoxified pertussis toxin, (vii) filamentous hemagglutinin, (viii) pertactin, (ix) an antigen from a poliovirus Type 1 strain, (x) an antigen from a poliovirus Type 2 strain and (xi) an antigen from a poliovirus Type 3 strain.
- (i) a conjugate that is a capsular saccharide from GBS serotype Ia conjugated to a carrier protein, (ii) a conjugate that is a capsular saccharide from GBS serotype Ib conjugated to a carrier protein, (iii) a conjugate that is a capsular saccharide from GBS serotype III conjugated to a carrier protein, (iv) a diphtheria toxoid, (v) a tetanus toxoid, (vi) acellular pertussis antigen, (vii) an antigen from a poliovirus Type 1 strain, (viii) an antigen from a poliovirus Type 2 strain and (ix) an antigen from a poliovirus Type 3 strain.

Typically, the carrier protein in the GBS conjugate comprising a capsular saccharide from GBS serotype Ia capsular saccharide, the carrier protein in the GBS conjugate comprising GBS serotype Ib capsular saccharide and the carrier portion in the GBS conjugate comprising GBS serotype III capsular saccharide is CRM197.

Further exemplary immunogenic composition of the invention include:

A composition which comprises (a) a conjugate that is a capsular saccharide from GBS serotype Ia conjugated to CRM197; b) a conjugate that is a capsular saccharide from GBS serotype Ib conjugated to CRM197; c) a conjugate that is a capsular saccharide from GBS serotype III conjugated to CRM197 and (d) diphtheria toxoid, particularly diphtheria toxoid prepared by treatment of diphtheria toxin with formaldehyde, particularly diphtheria toxoid wherein the diphtheria toxoid is not conjugated to a GBS capsular polysaccharide.

A composition which comprises (a) a conjugate that is a capsular saccharide from GBS serotype Ia conjugated to CRM197; b) a conjugate that is a capsular saccharide from GBS serotype Ib conjugated to CRM197; c) a conjugate that is a capsular saccharide from GBS serotype III conjugated to CRM197 and (d) tetanus toxoid, particularly wherein the tetanus toxoid is not conjugated to a GBS capsular polysaccharide.

A composition which comprises (a) a conjugate that is a capsular saccharide from GBS serotype Ia conjugated to CRM197; b) a conjugate that is a capsular saccharide from GBS serotype Ib conjugated to CRM197; c) a conjugate that is a capsular saccharide from GBS serotype III conjugated to CRM197; (d) diphtheria toxoid, particularly diphtheria toxoid prepared by treatment of diphtheria toxin with formaldehyde, particularly diphtheria toxoid wherein the diphtheria toxoid is not conjugated to a GBS capsular polysaccharide and (e) tetanus toxoid, particularly wherein the tetanus toxoid is not conjugated to a GBS capsular polysaccharide.

A composition which comprises (a) a conjugate that is a capsular saccharide from GBS serotype Ia conjugated to CRM197; b) a conjugate that is a capsular saccharide from GBS serotype Ib conjugated to CRM197; c) a conjugate that is a capsular saccharide from GBS serotype III conjugated to CRM197; (d) diphtheria toxoid, particularly diphtheria toxoid prepared by treatment of diphtheria toxin with formaldehyde, particularly diphtheria toxoid wherein the diphtheria toxoid is not conjugated to a GBS capsular polysaccharide; (e) tetanus toxoid, particularly wherein the tetanus toxoid is not conjugated to a GBS capsular polysaccharide and (f) a cellular pertussis antigen or an acellular pertissus antigen.

A composition which comprises (a) a conjugate that is a capsular saccharide from GBS serotype Ia conjugated to CRM197; b) a conjugate that is a capsular saccharide from GBS serotype Ib conjugated to CRM197; c) a conjugate that is a capsular saccharide from GBS serotype III conjugated to CRM197; (d) diphtheria toxoid, particularly diphtheria toxoid prepared by treatment of diphtheria toxin with formaldehyde, particularly diphtheria toxoid wherein the diphtheria toxoid is not conjugated to a GBS capsular polysaccharide; (e) tetanus toxoid, particularly wherein the tetanus toxoid is not conjugated to a GBS capsular polysaccharide; (f) detoxified pertussis toxin, (g) filamentous hemagglutinin; (h) pertactin and optionally (i) an inactivated polio virus antigen.

A composition which comprises (a) a conjugate that is a capsular saccharide from GBS serotype Ia conjugated to CRM197; b) a conjugate that is a capsular saccharide from GBS serotype Ib conjugated to CRM197; c) a conjugate that is a capsular saccharide from GBS serotype III conjugated to CRM197; d) a conjugate that is a capsular saccharide from GBS serotype II conjugated to CRM197; and e) a conjugate that is a capsular saccharide from GBS serotype V conjugated to CRM197; (f) diphtheria toxoid, particularly diphtheria toxoid prepared by treatment of diphtheria toxin with formaldehyde, particularly diphtheria toxoid wherein the diphtheria toxoid is not conjugated to a GBS capsular polysaccharide and/or (g) tetanus toxoid, particularly wherein the tetanus toxoid is not conjugated to a GBS capsular polysaccharide; optionally (h) a cellular pertussis antigen or an acellular pertissus antigen; optionally (i) detoxified pertussis toxin; optionally (j) filamentous hemagglutinin; optionally (k) pertactin and optionally (l) an inactivated polio virus antigen.

A composition which comprises (a) a conjugate that is a capsular saccharide from GBS serotype Ia conjugated to CRM197; b) a conjugate that is a capsular saccharide from GBS serotype Ib conjugated to CRM197; c) a conjugate that is a capsular saccharide from GBS serotype III conjugated to CRM197; d) a conjugate that is a capsular saccharide from GBS serotype II conjugated to CRM197 or tetanus toxoid; and e) a conjugate that is a capsular saccharide from GBS serotype V conjugated to CRM197 or tetanus toxoid; (f) diphtheria toxoid, particularly diphtheria toxoid prepared by treatment of diphtheria toxin with formaldehyde, particularly diphtheria toxoid wherein the diphtheria toxoid is not conjugated to a GBS capsular polysaccharide and/or (g) tetanus toxoid, particularly wherein the tetanus toxoid is not conjugated to a GBS capsular polysaccharide; optionally (h) a cellular pertussis antigen or an acellular pertissus antigen; optionally (i) detoxified pertussis toxin; optionally (j) filamentous hemagglutinin; optionally (k) pertactin and optionally (l) an inactivated polio virus antigen.

Pharmaceutical Methods and Uses

The immunogenic compositions of the invention may further comprise a pharmaceutically acceptable carrier. Typical 'pharmaceutically acceptable carriers' include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose [81], trehalose [82], lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable excipients is available in reference 83.

Compositions of the invention may be in aqueous form (i.e. solutions or suspensions) or in a dried form (e.g. lyophilised). If a dried vaccine is used then it will be reconstituted into a liquid medium prior to injection. Lyophilisation of conjugate vaccines is known in the art e.g. the MENJUGATE™ product is presented in lyophilised form. When the immunogenic compositions of the invention include conjugates comprising capsular saccharides from more than one GBS serotypes, it is typical for the conjugates to be prepared separately, mixed and then lyophilised. In this way, lyophilised compositions comprising two, three or four etc. conjugates as described herein may be prepared.

To stabilise conjugates during lyophilisation, non-active components, e.g. as stabilizers, can be added prior to freeze-drying. Preferred stabilizers for inclusion are lactose, sucrose and mannitol, as well as mixtures thereof e.g. lactose/sucrose mixtures, sucrose/mannitol mixtures, etc. A final vaccine obtained by aqueous reconstitution of the lyophilised material may thus contain lactose and/or sucrose. It is preferred to use amorphous excipients and/or amorphous buffers when preparing lyophilised vaccines [84].

It may be preferred to include a sugar alcohol (e.g. mannitol) and/or a disaccharide (e.g. sucrose or trehalose) e.g. at between 1 mg/ml and 30 mg/ml (e.g. about 25 mg/ml) in the composition. The use of sucrose has been recommended as a stabiliser for GBS conjugate vaccines (ref. 85). However, it is typical for the stabiliser of the present invention to be mannitol. When the dried vaccine is reconstituted into a liquid medium prior to injection, the concentration of residual mannitol will typically be about 2-20 mg/ml, e.g. 3.75 mg/ml, 7.5 mg/ml or 15 mg/ml.

Compositions may be presented in vials, or they may be presented in ready-filled syringes. The syringes may be supplied with or without needles. A syringe will include a single dose of the composition, whereas a vial may include a single dose or multiple doses.

Compositions of the invention are preferably administered to patients in 0.5 ml unit doses. References to 0.5 ml doses will be understood to include normal variance e.g. 0.5 ml+0.05 ml. For multidose situations, multiple dose amounts will be extracted and packaged together in a single container e.g. 5 ml for a 10-dose multidose container (or 5.5 ml with 10% overfill).

Aqueous compositions of the invention are also suitable for reconstituting other vaccines from a lyophilised form. Where a composition of the invention is to be used for such extemporaneous reconstitution, the invention provides a kit, which may comprise two vials, or may comprise one ready-filled syringe and one vial, with the contents of the syringe being used to reactivate the contents of the vial prior to injection.

Vaccines can also be prepared in a form where the vaccine can be prepared extemporaneously at the time/point of use by mixing together two components. Such two-component embodiments include liquid/liquid mixing and liquid/solid mixing e.g. by mixing aqueous material with lyophilised material.

Thus, a kit useful for the invention comprises a first component comprising one or more GBS conjugates; and a second component comprising one or more antigens selected from: a) cellular or acellular pertussis antigen, b) a tetanus toxoid, c) a diphtheria toxoid and d) an inactivated polio virus antigen; wherein the two components are in separate containers (e.g. vials and/or syringes). The GBS conjugates in the first component may be lyophilised. In some embodiments, the first component does not comprise an adjuvant. The second component may comprise aqueous antigens. In some embodiments, the second component comprises an adjuvant, for example, an aluminium salt adjuvant.

Another kit useful for the invention may comprise a first component that is antigen-free, such that all antigenic components in the final immunogenic composition are derived from the second component. For example, a kit may comprise a first component comprising aqueous antigens comprising: (i) one or more GBS conjugates and (ii) one or more antigens selected from: a) cellular or acellular pertussis antigen, b) a tetanus toxoid, c) a diphtheria toxoid and d) an inactivated polio virus antigen; and a second component comprising aqueous adjuvant. The immunogenic composition of the invention can be prepared by mixing the first component and the second component.

The invention also provides a process for preparing the immunogenic composition of the invention, comprising mixing a first component comprising one or more GBS conjugates and a second component comprising one or more antigens selected from: a) cellular or acellular pertussis antigen, b) a tetanus toxoid, c) a diphtheria toxoid and d) an inactivated polio virus antigen. The GBS conjugates in the first component may be lyophilised. The second component may comprise aqueous antigens. The process may comprise a further step of reconstituting the lyophilised GBS conjugates in the first component with the aqueous antigens of the second component. The first component may not comprise an adjuvant. The second component may comprise an adjuvant, for example, an aluminium salt adjuvant.

Compositions of the invention may be packaged in unit dose form or in multiple dose form. For multiple dose forms, vials are preferred to pre-filled syringes. Effective dosage volumes can be routinely established, but a typical human dose of the composition has a volume of 0.5 ml e.g. for intramuscular injection.

The pH of the composition is preferably between 6 and 8, preferably about 7. Stable pH may be maintained by the use of a buffer. Aqueous compositions administered to a patient can have a pH of between 5.0 and 7.5, and more typically between 5.0 and 6.0 for optimum stability; where a diphtheria toxoid and/or tetanus toxoid is present, the pH is ideally between 6.0 and 7.0.

The immunogenic compositions of the invention typically comprise a potassium dihydrogen phosphate buffer. The potassium dihydrogen phosphate buffer may comprise about 1-10 mM potassium dihydrogen phosphate, e.g. 1.25 mM, 2.5 mM or 5.0 mM. If a composition comprises an aluminium hydroxide salt, it is preferred to use a histidine buffer [86]. The composition may be sterile and/or pyrogen-free. Compositions of the invention may be isotonic with respect to humans.

Compositions of the invention are immunogenic, and are more preferably vaccine compositions. Vaccines according to the invention may either be prophylactic (i.e. to prevent infection) or therapeutic (i.e. to treat infection), but will typically be prophylactic. Prophylactic vaccines do not guarantee complete protection from disease because even if the patient develops antibodies, there may be a lag or delay before the immune system is able to fight off the infection. Therefore, and for the avoidance of doubt, the term prophylactic vaccine may also refer to vaccines that ameliorate the effects of a future infection, for example by reducing the severity or duration of such an infection.

The terms "protection against infection" and/or "provide protective immunity" means that the immune system of a subject has been primed (e.g by vaccination) to trigger an immune response and repel infection. Particularly, the immune response triggered is capable of repelling infection against a number of pathogens, such as different strains of bacteria. A vaccinated subject may thus get infected, but is better able to repel the infection than a control subject. Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. Commonly, the desired result is the production of an antigen (e.g., pathogen)-specific immune response that is capable of or contributes to protecting the subject against the pathogen. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined rough routine trials.

The compositions of the invention may be prepared in various forms. For example, the compositions may be prepared as injectables, either as liquid solutions or suspensions. The composition may be prepared for pulmonary administration e.g. as an inhaler, using a fine powder or a spray. The composition may be prepared as a suppository or pessary. The composition may be prepared for nasal, aural or ocular administration e.g. as spray, drops, gel or powder [e.g. refs 87 & 88]. Success with nasal administration of pneumococcal saccharides [89,90], Hib saccharides [91], MenC saccharides [92], and mixtures of Hib and MenC saccharide conjugates [93] has been reported.

Compositions of the invention may include an antimicrobial, particularly when packaged in multiple dose format.

Compositions of the invention may comprise detergent e.g. a TWEEN™ (polysorbate), such as TWEEN™ 80. Detergents are generally present at low levels e.g. <0.01%.

Compositions of the invention may include sodium salts (e.g. sodium chloride) to give tonicity. A concentration of 10+2 mg/ml NaCl is typical. In some embodiments, a concentration of 4-10 mg/ml NaCl may be used, e.g. 9.0, 7.0, 6.75 or 4.5 mg/ml.

Compositions will generally have an osmolality of between 200 mOsm/kg and 400 mOsm/kg, preferably between 240-360 mOsm/kg, and will more preferably fall within the range of 280-320 mOsm/kg. Osmolality has previously been reported not to have an impact on pain caused by vaccination [94], but keeping osmolality in this range is nevertheless preferred.

Compositions of the invention will generally include a buffer. A phosphate buffer is typical.

Compositions of the invention may be administered in conjunction with other immunoregulatory agents. In particular, compositions may include one or more adjuvants. Such adjuvants include, but are not limited to:

A. Mineral-Containing Compositions

Mineral containing compositions suitable for use as adjuvants in the invention include mineral salts, such as aluminium salts and calcium salts (or mixtures thereof). Calcium salts include calcium phosphate (e.g. the "CAP" particles disclosed in ref. 95). Aluminium salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt [96].

The adjuvants known as aluminium hydroxide and aluminium phosphate may be used. These names are conventional, but are used for convenience only, as neither is a precise description of the actual chemical compound which is present (e.g. see chapter 9 of reference 97). The invention can use any of the "hydroxide" or "phosphate" adjuvants that are in general use as adjuvants. The adjuvants known as "aluminium hydroxide" are typically aluminium oxyhydroxide salts, which are usually at least partially crystalline. The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt.

A fibrous morphology (e.g. as seen in transmission electron micrographs) is typical for aluminium hydroxide adjuvants. The pI of aluminium hydroxide adjuvants is typically about 11 i.e. the adjuvant itself has a positive surface charge at physiological pH. Adsorptive capacities of between 1.8-2.6 mg protein per mg $Al^{+++}$ at pH 7.4 have been reported for aluminium hydroxide adjuvants.

Aluminium phosphate adjuvants generally have a $PO_4/Al$ molar ratio between 0.3 and 1.2, preferably between 0.8 and 1.2, and more preferably 0.95+0.1. The aluminium phosphate will generally be amorphous, particularly for hydroxyphosphate salts. A typical adjuvant is amorphous aluminium hydroxyphosphate with $PO_4/Al$ molar ratio between 0.84 and 0.92, included at 0.6 mg $Al^{3+}$/ml. The aluminium phosphate will generally be particulate (e.g. plate-like morphology as seen in transmission electron micrographs). Typical diameters of the particles are in the range 0.5-20 μm (e.g. about 5-10 μm) after any antigen adsorption. Adsorptive capacities of between 0.7-1.5 mg protein per mg $Al^{+++}$ at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

Suspensions of aluminium salts used to prepare compositions of the invention may contain a buffer (e.g. a phosphate or a histidine or a Tris buffer), but this is not always necessary. The suspensions are preferably sterile and pyrogen-free. A suspension may include free aqueous phosphate ions e.g. present at a concentration between 1.0 and 20 mM, preferably between 5 and 15 mM, and more preferably about 10 mM. The suspensions may also comprise sodium chloride.

The invention can use a mixture of both an aluminium hydroxide and an aluminium phosphate. In this case there may be more aluminium phosphate than hydroxide e.g. a weight ratio of at least 2:1 e.g. >5:1, >6:1, >7:1, >8:1, >9:1, etc.

The concentration of $Al^{+++}$ in a composition for administration to a patient is preferably less than 10 mg/ml e.g. <5 mg/ml, <4 mg/ml, <3 mg/ml, <2 mg/ml, <1 mg/ml, etc. A preferred range is between 0.3 and 1 mg/ml. A maximum of 0.85 mg/dose is preferred.

A typical adjuvant aluminium phosphate adjuvant is amorphous aluminium hydroxyphosphate with $PO_4/Al$ molar ratio between 0.84 and 0.92, included at 0.6 mg $Al^{3+}$/ml. Adsorption with a low dose of aluminium phosphate may be used e.g. between 50 and 100 μg $Al^{3+}$ per conjugate per dose.

B. Saponin Formulations [Chapter 22 of Ref. 97]

Saponin formulations may also be used as adjuvants in the invention. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 98. Saponin formulations may also comprise a sterol, such as cholesterol [99].

Combinations of saponins and cholesterols can be used to form unique particles called immunostimulating complexes (ISCOMs) [chapter 23 of ref. 97]. ISCOMs typically also include a phospholipid such as phosphatidylethanolamine or phosphatidylcholine. Any known saponin can be used in ISCOMs. Preferably, the ISCOM includes one or more of QuilA, QHA and QHC. ISCOMs are further described in refs. 99-101. Optionally, the ISCOMS may be devoid of additional detergent(s) [102].

A review of the development of saponin based adjuvants can be found in refs. 103 & 104.

C. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed in refs. 105-110. Virosomes are discussed further in, for example, ref. 111

D. Bacterial or Microbial Derivatives

Adjuvants suitable for use in the invention include bacterial or microbial derivatives such as immunostimulatory oligonucleotides and ADP-ribosylating toxins and detoxified derivatives thereof. Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 112, 113 and 114 disclose possible analog substitutions e.g. replacement of guanosine with 2'-deoxy-7-deazaguanosine. The adjuvant effect of CpG oligonucleotides is further discussed in refs. 115-120.

The CpG sequence may be directed to TLR9, such as the motif GTCGTT or TTCGTT [121]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 122-124. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 121 & 125-127.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 128 and as parenteral adjuvants in ref. 129. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 130-137. Numerical reference for amino acid substitutions is preferably based on the alignments of the A and B subunits of ADP-ribosylating toxins set forth in ref. 138, specifically incorporated herein by reference in its entirety.

E. Human Immunomodulators

Human immunomodulators suitable for use as adjuvants in the invention include cytokines, such as interleukins (e.g. IL-1, IL-2, IL-4, IL-5, IL-6, IL-7, IL-12 [139], etc.) [140], interferons (e.g. interferon-γ), macrophage colony stimulating factor, and tumor necrosis factor.

F. Bioadhesives and Mucoadhesives

Bioadhesives and mucoadhesives may also be used as adjuvants in the invention. Suitable bioadhesives include esterified hyaluronic acid microspheres [141] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [142].

G. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

H. Liposomes (Chapters 13 & 14 of ref. 97)

Examples of liposome formulations suitable for use as adjuvants are described in refs. 143-145.

I. Polyoxyethylene Ether and Polyoxyethylene Ester Formulations

Adjuvants suitable for use in the invention include polyoxyethylene ethers and polyoxyethylene esters [146]. Such formulations further include polyoxyethylene sorbitan ester surfactants in combination with an octoxynol [147] as well as polyoxyethylene alkyl ethers or ester surfactants in combination with at least one additional non-ionic surfactant such as an octoxynol [148]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

J. Polyphosphazene (PCPP)

PCPP formulations are described, for example, in refs. 149 and 150.

K. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

L. Imidazoquinolone Compounds.

Examples of imidazoquinolone compounds suitable for use adjuvants in the invention include Imiquamod and its homologues (e.g. "Resiquimod 3M"), described further in refs. 151 and 152.

M. Thiosemicarbazone Compounds.

Examples of thiosemicarbazone compounds, as well as methods of formulating, manufacturing, and screening for compounds all suitable for use as adjuvants in the invention include those described in ref. 153. The thiosemicarbazones are particularly effective in the stimulation of human peripheral blood mononuclear cells for the production of cytokines, such as TNF-α.

N. Tryptanthrin Compounds.

Examples of tryptanthrin compounds, as well as methods of formulating, manufacturing, and screening for compounds all suitable for use as adjuvants in the invention include those described in ref. 154. The tryptanthrin compounds are particularly effective in the stimulation of human peripheral blood mononuclear cells for the production of cytokines, such as TNF-α.

The invention may also comprise combinations of aspects of one or more of the adjuvants identified above.

Other substances that act as immunostimulating agents are disclosed in chapter 7 of ref. 97.

The use of aluminium salt adjuvants is particularly preferred, and antigens are generally adsorbed to such salts. It is possible in compositions of the invention to adsorb some antigens to an aluminium hydroxide but to have other antigens in association with an aluminium phosphate. In general, however, it is preferred to use only a single salt e.g. a hydroxide or a phosphate, but not both. Not all conjugates need to be adsorbed i.e. some or all can be free in solution.

Methods of Treatment

The invention also provides a method for raising an immune response in a mammal, comprising administering a pharmaceutical composition of the invention to the mammal. The immune response is preferably protective and preferably involves antibodies. The method may raise a booster response. Compositions of the invention are preferably administered to patients in 0.5 ml doses (as discussed above).

The mammal is preferably a human. Where the vaccine is for prophylactic use, the human is preferably a child (e.g. a toddler or infant, particularly a neonate) or a teenager; where the vaccine is for therapeutic use, the human is preferably an adult. A vaccine intended for children may also be administered to adults e.g. to assess safety, dosage, immunogenicity, etc. A preferred class of humans for treatment are females of child-bearing age (e.g. teenagers and above). Another preferred class is pregnant females. Elderly patients (e.g. those above 50, 60, 70, 80 or 90 etc. years of age, particularly over 65 years of age), especially those living in nursing homes where the risk of GBS infection may be increased ([155]), are another preferred class of humans for treatment.

In some embodiments, the patient has been pre-immunised with a diphtheria toxoid or derivative thereof. In other embodiments, the patient has been pre-immunised with a tetanus toxoid or derivative thereof.

The invention also provides a composition of the invention for use as a medicament. The medicament is preferably able to raise an immune response in a mammal (i.e. it is an immunogenic composition) and is more preferably a vaccine.

The invention also provides the use of a composition of the invention in the manufacture of a medicament for raising an immune response in a mammal.

These uses and methods are preferably for the prevention and/or treatment of a disease caused by *Streptococcus agalactiae* and one or more of *Corynebacterium diphtheriae, Clostridium tetani, Bordetella pertussis* and Poliovirus. A disease caused by *S. agalactiae* can be neonatal sepsis or bacteremia, neonatal pneumonia, neonatal meningitis, endometritis, osteomyelitis, septic arthritis, etc. *C. diphtheria* can cause diphtheria; *C. tetani* can cause tetanus; *B. pertussis* can cause whooping cough; and Poliovirus can cause polio.

The subject in which disease is prevented may not be the same as the subject that receives the immunogenic composition of the invention. For instance, an immunogenic composition may be administered to a female (before or during pregnancy) in order to protect offspring (so-called 'maternal immunization' [156-158]). The immunization of the pregnant female provides antibody-mediated immunity to the infant through passive maternal immunity. The passive immunity occurs naturally when maternal antibodies are transferred to the fetus through the placenta. Passive immunity is especially important to infants because they are born without any actively acquired immunity. Administration of compositions of the invention to a pregnant female enhances immunity in the female, and antibodies are passed to the newborn through the placenta, conferring passive maternal immunity on the infant. However, passive immunity in infants is only temporary and starts to decrease after the first few weeks, or months of life. As passive immunity is only temporary, it may be important for the infant to receive administration of a composition of the invention, to induce active immunity in the infant, before the passive immunity diminishes. Administration of a second immunogenic composition to the infant after birth induces active immunity in the infant, and extends the immunity passed on from the mother during pregnancy.

As used herein, an infant is an individual under one year of age (e.g., less than one day old, 1 week old, 2 weeks old, 3 weeks old, 4 weeks old, 2 months old, 3 months, 4 months, 5 months, 6 months, 7 months, 8 months old, 9 months old, 10 months old, 11 months old, less than 12 months old).

The pregnant female may be administered the composition of the invention at any time during her pregnancy. For example, the composition may be administered to the female during the first, second or third trimester of her pregnancy. In some embodiments, the composition is administered to the female during the last 6-12 weeks of the pregnancy (e.g., 28 weeks gestation, 29 weeks gestation, 30 weeks gestation, 31 weeks gestation, 32 weeks gestation, 33 weeks gestation, 34 weeks gestation, 35 weeks gestation, 36 weeks gestation, 37 weeks gestation, 38 weeks gestation, 39 weeks gestation). Particularly, the composition of the invention is administered to the pregnant female at least four weeks before delivery of the infant. In some embodiments, a one-dose regimen is administered to the pregnant female between weeks 32 and 36 gestation. In other embodiments, a two-dose regimen is administered to the pregnant female, with the first dose being administered at approximately 32 weeks gestation and the second dose being administered at approximately 36 weeks gestation.

The infant may be administered the composition at any time during the first year of life, and thereafter if desired. Generally the composition will be administered to the infant one, two, three, four or more times during the first year of life. For example, the composition of the invention may be administered to the infant one or more times selected from at birth, at 2 weeks old, 4 weeks old, 6 weeks old, 2 months old, 3 months old, 4 months old, 6 months old, 9 months old, and 12 months old. Particularly, the composition of the invention is administered to the infant at a time before maternal antibodies have decreased to non-protective titers. Subsequent administrations can occur on any desired schedule.

In one embodiment, there is provided a method of protecting an infant against a disease caused by *Streptococcus agalactiae* and one or more of *Corynebacterium diphtheriae, Clostridium tetani, Bordetella pertussis* and Poliovirus comprising the steps of (a) administering a composition of the invention to a female during pregnancy with said infant; and (b) optionally administering a composition of the invention to the infant that is born from the pregnancy.

Thus, there is also provided a method of protecting an infant against a disease caused by *S. agalactiae* and one or more of diphtheria, tetanus, whooping cough and polio comprising the steps of (a) administering a composition of the invention to a female during pregnancy with said infant; and (b) optionally administering a composition of the invention to the infant that is born from the pregnancy.

Preferred compositions of the invention can confer an antibody titre in a patient that is superior to the criterion for seroprotection for each antigenic component for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%. Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 ml.

The invention may be used to elicit systemic and/or mucosal immunity.

The immunogenic compositions of the invention may be administered in single or multiple doses. Administration of a single dose is preferred in the invention. Alternatively, a further one unit dose followed by a first unit dose may be effective. Typically, the second (or third, fourth, fifth etc.) unit dose is identical to the first unit dose. Typically, the immunogenic compositions of the invention are administered in three unit doses. Typically, the immunogenic compositions of the invention will be administered intramuscularly, e.g. by intramuscular administration to the thigh or the upper arm.

Multiple doses may be used in a primary immunization schedule and/or in a booster immunization schedule. A primary dose schedule may be followed by a booster dose schedule. Suitable timing between priming doses (e.g. between 4-16 weeks), and between priming and boosting, can be routinely determined.

In order to have full efficacy, a typical primary immunization schedule (particularly for a child) may involve administering more than one dose. For example, doses may be at: 0 & 6 months (time 0 being the first dose); at 0, 1, 2 & 6 months; at day 0, day 21 and then a third dose between 6 & 12 months; at 2, 4 & 6 months; at 3, 4 & 5 months; at 6, 10 & 14 weeks; at 2, 3 & 4 months; or at 0, 1, 2, 6 & 12 months. Paediatric compositions can also be used as booster doses e.g. for children, in the second year of life.

Compositions can also be used as booster doses e.g. for children, in the second year of life. Adolescent booster vaccine compositions of the invention are administered in a single dose to persons of age 10 and older. The immunogenic composition of the invention can be administered as a booster vaccine to a patient who has previously been vaccinated against both diphtheria and tetanus, and preferably also against pertussis. These patients can be distinguished from the general population by having an immunological memory response against the previous vaccine. The patients may have received their most recent diphtheria and/or tetanus vaccines at least five years before receiving the vaccine of the invention. The patients receiving the vaccines may be aged between 4 and 65 years of age e.g. 11-64 years, 10-18 years, etc.

Any suitable route of administration can be used. For example, a composition can be administered intramuscularly, intraperitoneally, subcutaneously, transdermally, or intradermally. If desired, the composition can be administered through an intramucosal route such as intra-orally, intra-nasally, intra-vaginally, and intra-rectally. Administration to the pregnant female and the infant may be through the same route or different routes. Compositions of the invention can be administered by intramuscular injection e.g. into the arm or leg.

Vaccines produced by the invention may be administered to patients at the same time as a separate vaccine, e.g. at the same time as a pneumococcal conjugate vaccine such as PREVNAR™, at the same time as an influenza vaccine, at the same time as a rotavirus vaccine, at the same time as a MMR vaccine, etc.

Where compositions of the invention include an aluminium-based adjuvant, settling of components may occur during storage. The composition should therefore be shaken prior to administration to a patient. The shaken composition will be a turbid white suspension.

General

The term "comprising" encompasses "including" as well as "consisting" e.g. a composition "comprising" X may consist exclusively of X or may include something additional e.g. X+Y.

The term "consisting of" means "consisting only of". A composition "consisting of X" may not include any other components. A composition "consisting essentially of X" may not include any other active components. The term "consisting essentially of" means that the composition, method or structure may include additional ingredients, steps and/or parts, but only if the additional ingredients, steps and/or parts do no materially alter the basic and novel characteristics of the claimed composition, method or structure.

The term "about" in relation to a numerical value x means, for example, x+10%.

The word "substantially" does not exclude "completely" e.g. a composition which is "substantially free" from Y may be completely free from Y. Where necessary, the word "substantially" may be omitted from the definition of the invention.

It will be appreciated that sugar rings can exist in open and closed form and that, whilst closed forms are shown in structural formulae herein, open forms are also encompassed by the invention. Similarly, it will be appreciated that sugars can exist in pyranose and furanose forms and that, whilst pyranose forms are shown in structural formulae herein, furanose forms are also encompassed. Different anomeric forms of sugars are also encompassed.

Unless specifically stated, a process comprising a step of mixing two or more components does not require any specific order of mixing. Thus components can be mixed in any order. Where there are three components then two components can be combined with each other, and then the combination may be combined with the third component, etc.

Antibodies will generally be specific for their target. Thus they will have a higher affinity for the target than for an irrelevant control protein, such as bovine serum albumin.

The term "about" in relation to a numerical value x means, for example, x+10%.

Where a component is described as being "adsorbed" to an adjuvant, it is preferred that at least 50% (by weight) of that antigen is adsorbed e.g. 50%, 60%, 70%, 80%, 90%, 95%, 98% or more. If a component is totally adsorbed then none should detectable in the supernatant of a composition after centrifugation.

Unless specifically stated, a process comprising a step of mixing two or more components does not require any specific order of mixing. Thus components can be mixed in any order. Where there are three components then two components can be combined with each other, and then the combination may be combined with the third component, etc.

Amounts of conjugates are generally given in terms of mass of saccharide (i.e. the dose of the conjugate (carrier+ saccharide) as a whole is higher than the stated dose) in order to avoid variation due to choice of carrier.

Phosphorous-containing groups employed with the invention may exist in a number of protonated and deprotonated forms depending on the pH of the surrounding environment, for example the pH of the solvent in which they are dissolved. Therefore, although a particular form may be illustrated herein, it is intended, unless otherwise mentioned, for these illustrations to merely be representative and not limiting to a specific protonated or deprotonated form. For example, in the case of a phosphate group, this has been illustrated as $-OP(O)(OH)_2$ but the definition includes the protonated forms $-[OP(O)(OH_2)(OH)]^+$ and $-[OP(O)(OH_2)_2]^{2+}$ that may exist in acidic conditions and the deprotonated forms $-[(OP(O)(OH)(O)]^-$ and $[OP(O)(O)_2]^{2-}$ that may exist in basic conditions. The invention encompasses all such forms.

Where a compound is administered to the body as part of a composition then that compound may alternatively be replaced by a suitable prodrug.

Where animal (and particularly bovine) materials are used in the culture of cells, they should be obtained from sources that are free from transmissible spongiform encephalopathies (TSEs), and in particular free from bovine spongiform encephalopathy (BSE).

MODES FOR CARRYING OUT THE INVENTION

Figure 1:
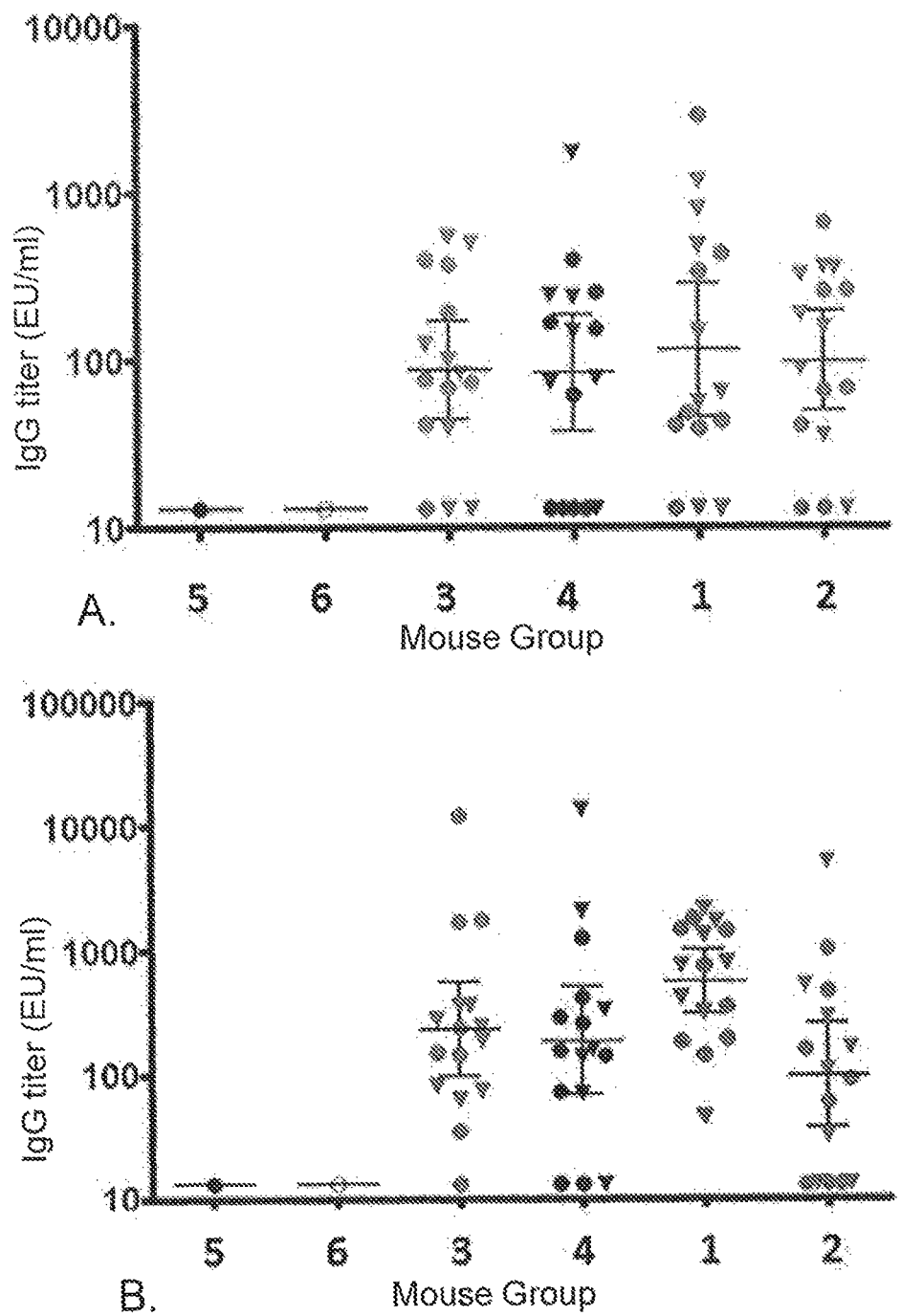
FIG. 1 shows IgG titers against (A) GBS Ia, (B) GBS Ib and (C) GBS III in the mouse groups described in Table 1. Sera were pooled for all mice in groups 5 and 6. GMT titers are indicated by the central bar. Upper and lower bars indicate 95% confidence intervals.
Figure 1:
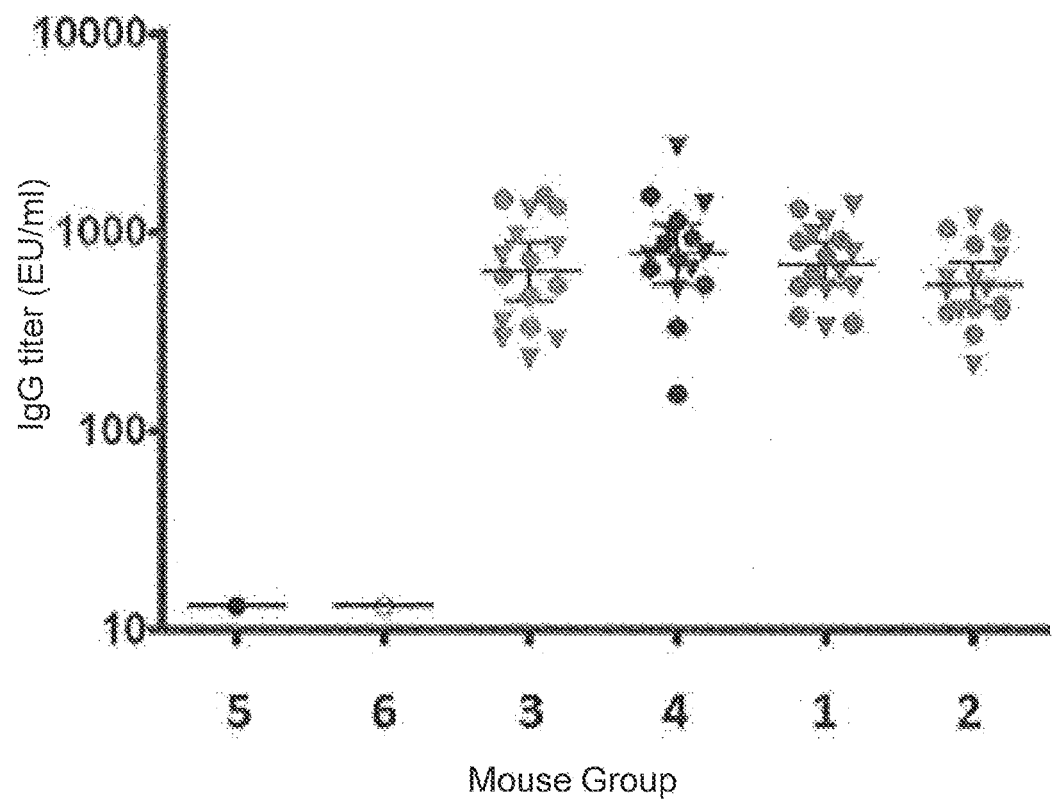

Materials and Methods
Vaccines

The GBS trivalent vaccine used in the following experiments is composed of capsular polysaccharides derived from three major serotypes: Ia, Ib and III, each conjugated to CRM197. The TdaP(H4) vaccine is adjuvanted with aluminium hydroxide and contains Tetanus toxoid, Diphtheria toxoid and Acellular Pertussis antigens (PT, FHA and 69K).

The TdaP(H4)-IPV vaccine is adjuvanted with aluminium hydroxide and contains Tetanus toxoid, Diphteria toxoid, Acellular Pertussis antigens (PT, FHA and 69K) and Polio antigens (IPV1, IPV2 and IPV3).

Commercially available Tetanus and Tetanus/Diphteria liquid vaccines were used.

ELISA

IgG titers against GBS polysaccharides Ia, Ib and III in the sera from immunized mice were measured by ELISA as explained in reference 159. Generally, there is good correlation between ELISA IgG Abs and OPK titers.

Opsonophagocytic Killing (OPK) Assay

Measuring the opsonizing activity of serum antibody is a useful indicator of vaccine activity since protection is likely afforded by opsonophagocytic killing. The opsonophagocytosis killing assay measures the ability of serum antibody to opsonize GBS for killing by effector cells in the presence of complement. OPK assays to measure the functional activity of antibodies elicited in immunized mice against GBS polysaccharides Ia, Ib and III were performed using HL-60, a pro-myelocytic leukemia cell line obtained from the American Type Culture Collection (ATCC, CCL-240). The strains GBS 515, GBS H36b and GBS COH1 were used to measure killing of serotype Ia, Ib and III isolates, respectively. Negative control reactions were performed either in the presence of heat inactivated complement or in the absence of antibody or effector cells, or using pre-immune or placebo sera. Reactions were plated in trypticase soy agar plate and bacterial counts were determined. The percentage of killing was calculated as (mean CFU at T0−mean CFU at T60)/(mean CFU at T0). OPK titers were expressed as the reciprocal serum dilution leading to 50% killing of bacteria. The OPK assay was performed according to the killing-based opsonophagocytosis assay (kOPA) protocol described in reference 160.

LUMINEX™ Based Multiplex Assay

A LUMINEX™-based multiplex assay for IgG quantification of tetanus, diphtheria and pertussis antigens was used. Diphteria Toxoid (DT), Tetanus Toxoid (TT), Pertussis Toxoid (PT), Pertussis FHA and Pertussis 69K antigens were each covalently conjugated to microspheres (Luminex Corporation, Austin, Tex.). Mouse serum samples were analyzed to assess antibody titers specific to each antigen. Experiments were performed in duplicate and values from duplicates were averaged. A reference serum was prepared by pooling sera from CD1 mice immunized with TdaP antigens+Alum.

Study 1: GBS Reconstituted in TdaP and TdAP-IPV

This study investigated the immunogenicity of lyophilized GBS trivalent vaccines (Ia, Ib, III polysaccharides conjugated to CRM197) reconstituted with: (i) Alum adjuvanted liquid vaccine containing Tetanus, Diphteria and Acellular Pertussis antigens (TdaP) and (ii) Alum adjuvanted liquid vaccine containing Tetanus, Diphteria, Acellular Pertussis and Polio antigens (TdaP-IPV).

The immunization protocol is reported in Table 1 and was repeated two times. In each experiment, six groups of 8 CD1 female mice were immunized intraperitoneally on days 0 and 21, with 2 doses of the vaccines shown in Table 1, and bled on days 0 and 35.

TABLE 1

Immunization protocol for study 1.

| Group N° | Vaccine Type | Vaccine composition | Volume route | Antigens Dose | Adjuvant Dose | N° mice |
|---|---|---|---|---|---|---|
| 1 | GBS + TdaP(H4) | PSIa-CRM 5 µg/ml<br>PSIb-CRM 5 µg/ml<br>PSIII-CRM 5 µg/ml<br>T 10 Lf/ml<br>D 8 Lf/ml<br>PT 8 µg/ml<br>FHA 8 µg/ml<br>69K 16 µg/ml<br>Alum 2 µg/ml | i.p. 200 µl | PSIa-CRM 1 µg<br>PSIb-CRM 1 µg<br>PSIII-CRM 1 µg<br>T 2 Lf<br>D 1.6 Lf<br>PT 1.6 µg<br>FHA 1.6 µg<br>69K 3.2 µg | Alum 400 µg | 8 |
| 2 | GBS + TdaP(H4)-IPV | PSIa-CRM 5 µg/ml<br>PSIb-CRM 5 µg/ml<br>PSIII-CRM 5 µg/ml<br>T 10 Lf/ml<br>D 8 Lf/ml<br>PT 8 µg/ml<br>FHA 8 µg/ml<br>69K 16 µg/ml<br>IPV1 80 dU/ml<br>IPV2 16 dU/ml<br>IPV3 64 dU/ml<br>Alum 2 mg/ml | i.p. 200 µl | PSIa-CRM 1 µg<br>PSIb-CRM 1 µg<br>PSIII-CRM 1 µg<br>T 2 Lf<br>D 1.6 Lf<br>PT 1.6 µg<br>FHA 1.6 µg<br>69K 3.2 µg<br>IPV1 16 dU<br>IPV2 3.2 dU<br>IPV3 12.8 dU | Alum 400 µg | 8 |
| 3 | GBS only | PSIa-CRM 5 µg/ml<br>PSIb-CRM 5 µg/ml<br>PSIII-CRM 5 µg/ml<br>Alum 2 mg/ml | i.p. 200 µl | PSIa-CRM 1 µg<br>PSIb-CRM 1 µg<br>PSIII-CRM 1 µg | Alum 400 µg | 8 |
| 4 | GBS only | PSIa-CRM 5 µg/ml<br>PSIb-CRM 5 µg/ml<br>PSIII-CRM 5 µg/ml<br>Alum 2 mg/ml | i.p. 200 µl | PSIa-CRM 1 µg<br>PSIb-CRM 1 µg<br>PSIII-CRM 1 µg | Alum 400 µg | 8 |
| 5 | No antigen | Alum 2 mg/ml | i.p. 200 µl | — | Alum 400 µg | 8 |

TABLE 1-continued

Immunization protocol for study 1.

| Group N° | Vaccine Type | Vaccine composition | Volume route | Antigens Dose | Adjuvant Dose | N° mice |
|---|---|---|---|---|---|---|
| 6 | TdaP(H4)-IPV | T 10 Lf/ml<br>D 8 Lf/ml<br>PT 8 μg/ml<br>FHA 8 μg/ml<br>69K 16 μg/ml<br>IPV1 80 dU/ml<br>IPV2 16 dU/ml<br>IPV3 64 dU/ml<br>Alum 2 mg/ml | i.p. 200 μl | T 2 Lf<br>D 1.6 Lf<br>PT 1.6 μg<br>FHA 1.6 μg<br>69K 3.2 μg<br>IPV1 16 dU<br>IPV2 3.2 dU<br>IPV3 12.8 dU | Alum<br>400 μg | 8 |

Sera from immunized mice were analyzed for the presence of IgG antibodies against each GBS serotype specific antigen (types Ia, Ib, and III) by ELISA. Antibodies against tetanus toxoid (TT), diphtheria toxoid (DT) and acellular pertussis antigens (PT, FHA and 69K) were quantified by LUMINEX™ assay. Functional activity of antibodies against GBS antigens was evaluated by opsonophagocytic killing (OPK) assay.

Figure 2:
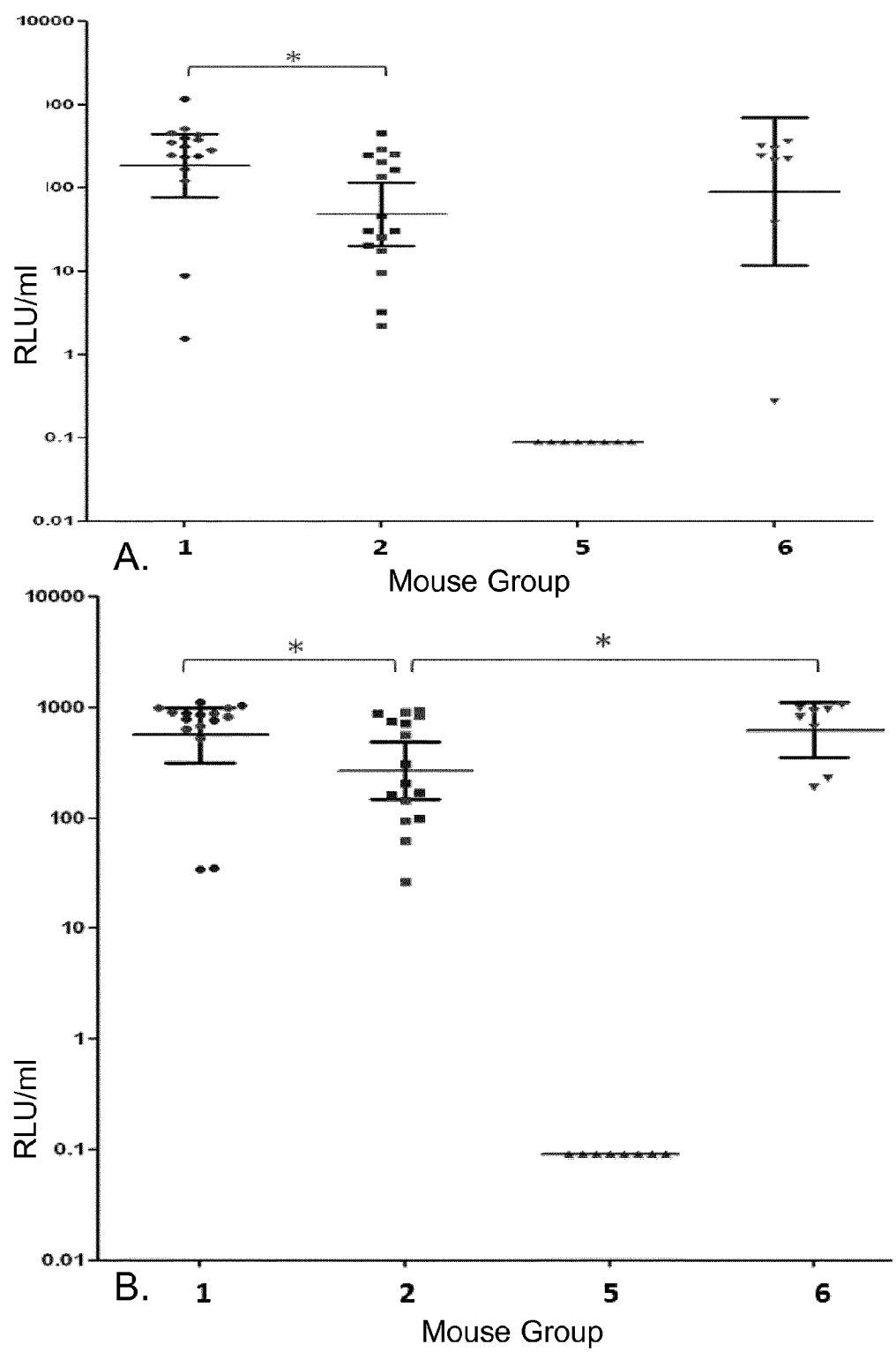
FIG. 2 shows IgG titers against (A) Diptheria Toxoid, (B) Tetanus Toxoid, (C) Pertussis Toxoid, (D) Pertussis FHA and (E) Pertussis 69K in mouse groups described in Table 1. Statistical significance is indicated by * ($p<0.05$). GMT titers are indicated by the central bar. Upper and lower bars indicate 95% confidence intervals.
Figure 2:
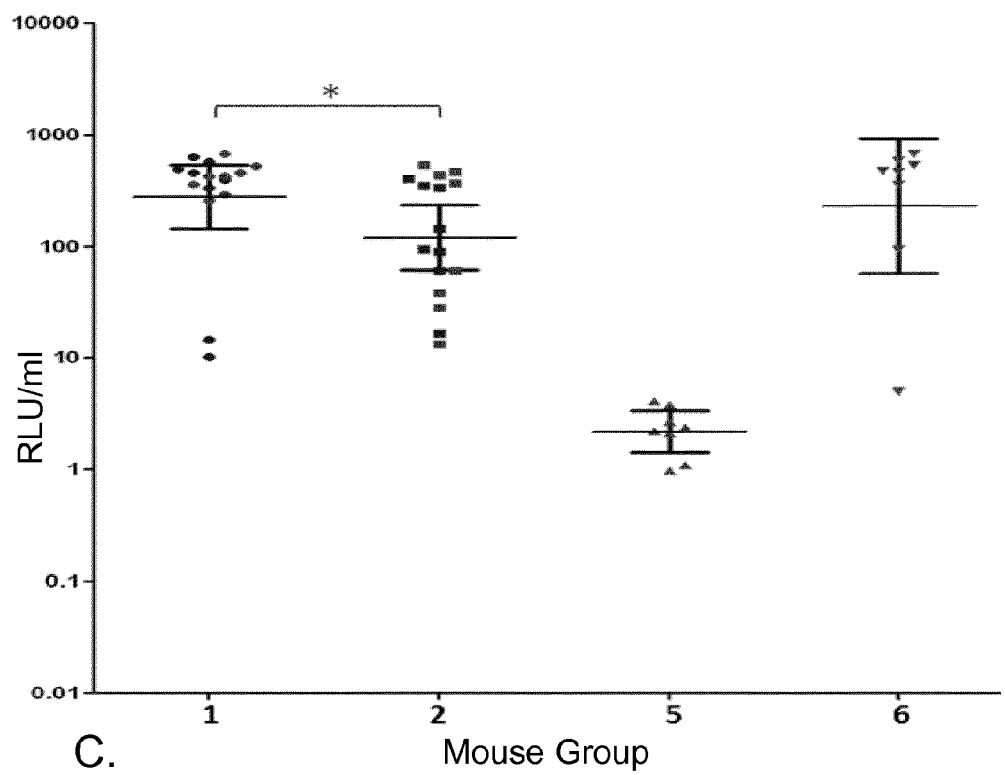
Figure 2:
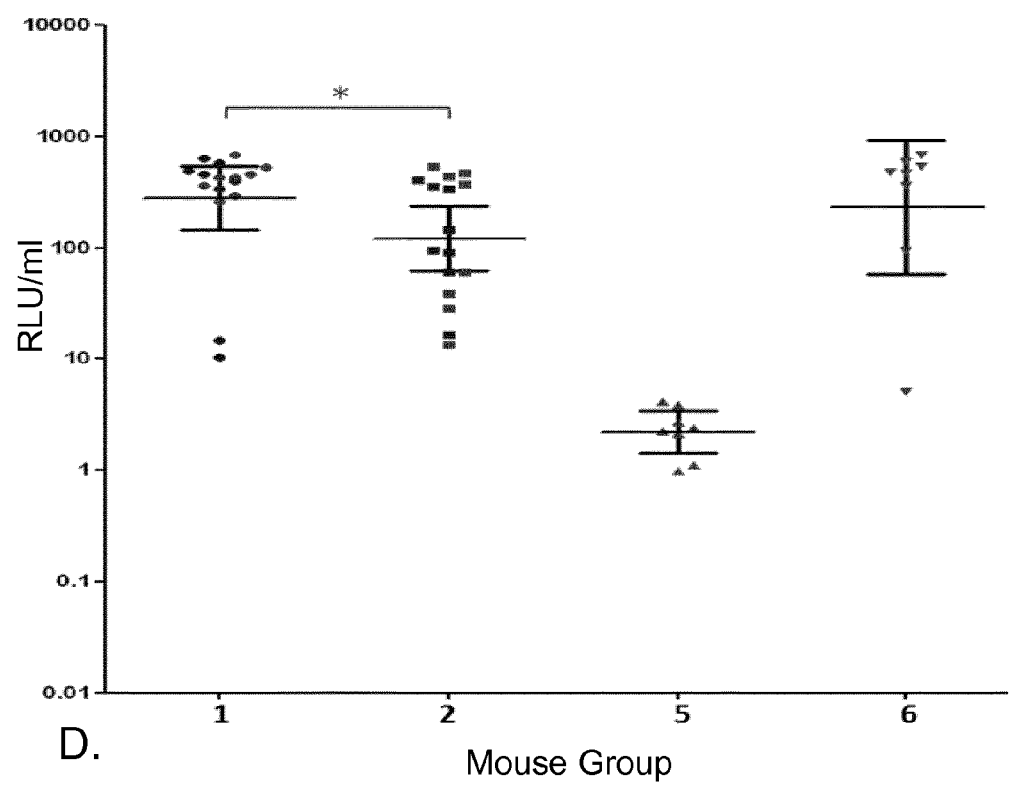
Figure 2:
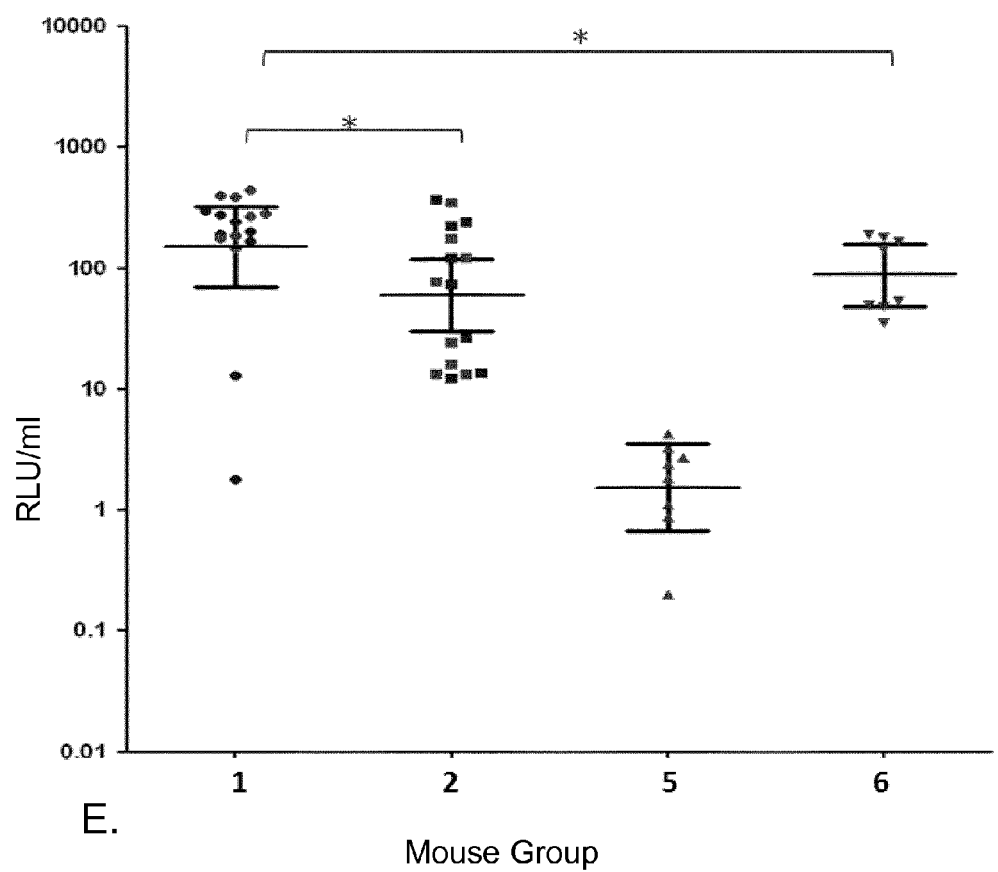

FIGS. 1 and 2 show the IgG titers against the various antigens of the six groups of mice tested in study 1 (merged results from 8+8 mice from the two experiments). The GMT titers are indicated in Table 2 below.

TABLE 2

GMT serum IgG titers after 2 immunizations in mice tested in study 1.

|  | Group 1 | Group 2 | Group 3 | Group 4 | Group 5 | Group 6 |
|---|---|---|---|---|---|---|
| GBS Ia | 112 | 97 | 87 | 82 | 13 | 13 |
| GBS Ib | 561 | 97 | 229 | 185 | 13 | 13 |
| GBS III | 683 | 537 | 625 | 762 | 13 | 13 |
| DT | 187.55 | 48.94 | N/A | N/A | <LLOQ | 89.95 |
| TT | 560.67 | 268.97 | N/A | N/A | <LLOQ | 626.72 |
| PT | 280.43 | 121.10 | N/A | N/A | 2.10 | 232.60 |
| FHA | 789.00 | 450.81 | N/A | N/A | <LLOQ | 749.95 |
| 69K | 789.0 | 450.8 | N/A | N/A | <LLOQ | 88.6 |

<LLOQ = below lower limit of quantification

Overall, all vaccine formulation provided immunogenicity that was comparable with the control, and no significant immunological interference was observed. For IgG titers post 2nd immunization against GBS Ia, Ib and III, no significant differences in Ig responses were detected by Mann-Whitney U test between the vaccine groups for any of the serotypes, indicating absence of interference. For IgG titers post 2nd immunization against DT, TT, PT, FHA and 69K, GBS+TDaP elicited about 2 fold higher GMT titers than GBS+TDaP+IPV ($P<0.05$ by Mann-Whitney U test), suggesting minor negative effects of IPV on all TDaP antigens. Additionally, for TT, the vaccine TDaP+IPV yielded 2 fold higher titers than TDaP+IPV+GBS (U test, $P<0.026$), suggesting minor negative effects of GBS on TT in the presence of IPV.

Figure 3:
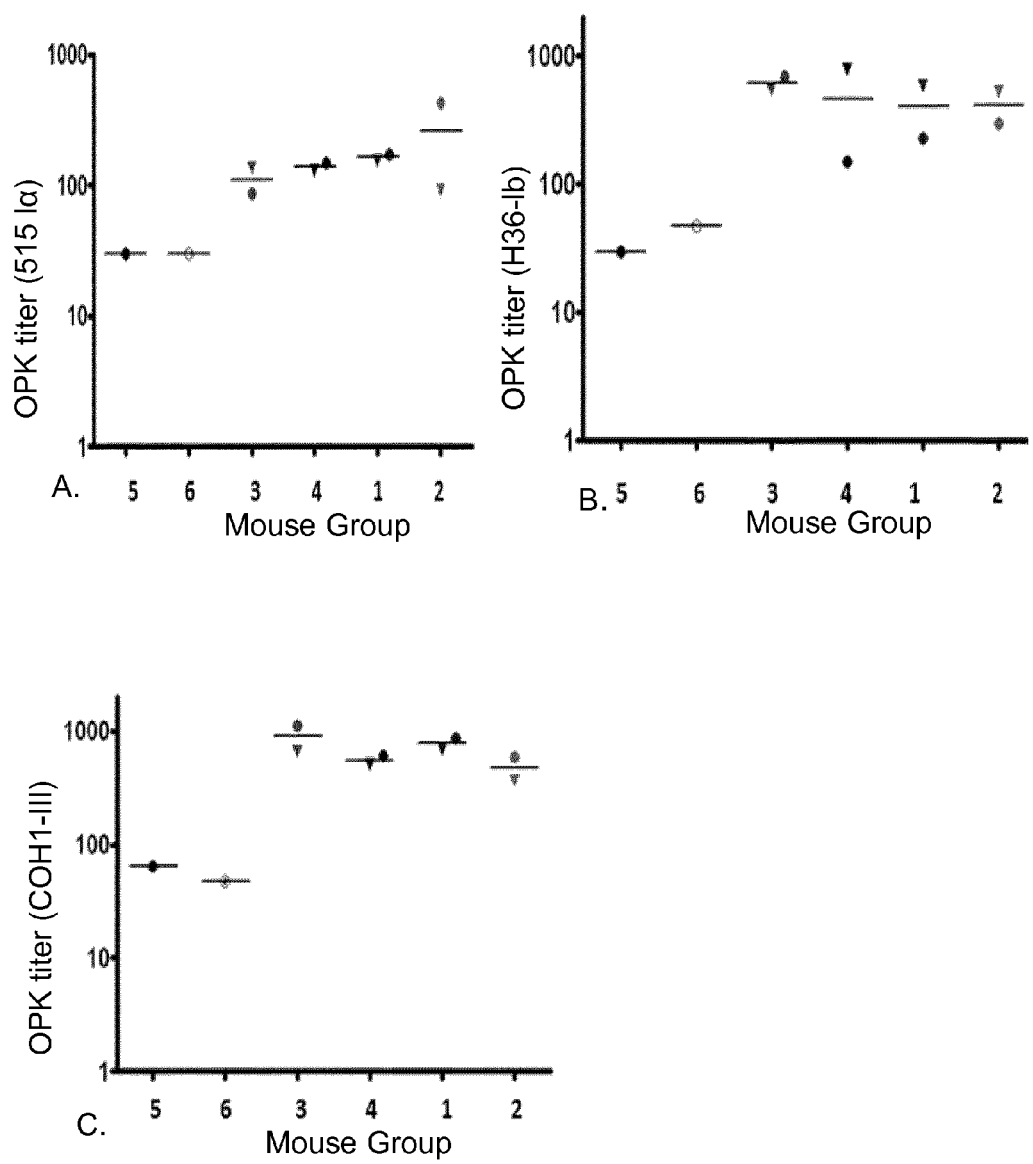
FIG. 3 shows OPK titers against (A) GBS Ia, (B) GBS Ib and (C) GBS III in the mouse groups described in Table 1. Sera were pooled from all mice in each group (except for groups 5 and 6) for each experiment (experiment repeated twice). Sera from both experiments were pooled for each of groups 5 and 6. GMT titers are indicated by the central bar.

FIG. 3 shows the OPK titers against GBS Ia, Ib and III of the six groups of animals tested in study 1. As shown, no major differences in OPK titers against GBS Ia, Ib or III (in the range of assay and biological variability) were detected for any of the vaccine formulations.

Study 2: GBS Reconstituted in TdaP

This study investigated the immunogenicity of different amounts of lyophilized GBS trivalent vaccines (Ia, Ib, III polysaccharides conjugated to CRM197) reconstituted with Alum adjuvanted liquid vaccine containing Tetanus, Diphteria and Acellular Pertussis antigens (TdaP).

Eight groups of 16 CD1 female mice were immunized subcutaneously on days 0, 21 and 35, with 3 doses of vaccines, and bled on days 0, 35 (post-2) and 49 (post-3). The immunization protocol is reported in Table 3.

TABLE 3

Immunization protocol for study 2.

| Group N° | Vaccine Type | Vaccine composition | Volume route | Antigens Dose | Adjuvant Dose | N° mice |
|---|---|---|---|---|---|---|
| 1 | GBS + TdaP(H2) | PSIa-CRM 5 μg/ml<br>PSIb-CRM 5 μg/ml<br>PSIII-CRM 5 μg/ml<br>T 10 Lf/ml<br>D 4 Lf/ml<br>PT 8 μg/ml<br>FHA 8 μg/ml<br>69K 16 μg/ml<br>Alum 2 mg/ml | s.c.<br>200 μl | PSIa-CRM 1 μg<br>PSIb-CRM 1 μg<br>PSIII-CRM 1 μg<br>T 2 Lf<br>D 0.8 Lf<br>PT 1.6 μg<br>FHA 1.6 μg<br>69K 3.2 μg | Alum<br>400 μg | 8 |
| 2 | TdaP(H2) | T 10 Lf/ml<br>D 4 Lf/ml<br>PT 8 μg/ml<br>FHA 8 μg/ml<br>69K 16 μg/ml<br>Alum 2 mg/ml | s.c.<br>200 μl | T 2 Lf<br>D 0.8 Lf<br>PT 1.6 μg<br>FHA 1.6 μg<br>69K 3.2 μg | Alum<br>400 μg | 8 |

TABLE 3-continued

Immunization protocol for study 2.

| Group N° | Vaccine Type | Vaccine composition | Volume route | Antigens Dose | Adjuvant Dose | N° mice |
|---|---|---|---|---|---|---|
| 3 | GBS + TdaP(L2) | PSIb-CRM 0.25 µg PSIII-CRM 5 µg/ml T 10 Lf/ml D 4 Lf/ml PT 2 µg/ml FHA 2 µg/ml 69K 4 µg/ml Alum 2 mg/ml | s.c. 200 µl | PSIII-CRM 0.25 µg T 2 Lf D 0.8 Lf PT 0.4 µg FHA 0.4 µg 69K 0.8 µg | Alum 400 µg | 8 |
| 4 | TdaP(L2) | T 10 Lf/ml D 4 Lf/ml PT 2 µg/ml FHA 2 µg/ml 69K 4 µg/ml Alum 2 mg/ml | s.c. 200 µl | T 2 Lf D 0.8 Lf PT 0.4 µg FHA 0.4 µg 69K 0.8 µg | Alum 400 µg | 8 |
| 5 | GBS (H) | PSIa-CRM 5 µg/ml PSIb-CRM 5 µg/ml PSIII-CRM 5 µg/ml Alum 2 mg/ml | s.c. 200 µl | PSIa-CRM 1 µg PSIb-CRM 1 µg PSIII-CRM 1 µg | Alum 400 µg | 8 |
| 6 | GBS (L) | PSIa-CRM 5 µg/ml PSIb-CRM 5 µg/ml PSIII-CRM 5 µg/ml | s.c. 200 µl | PSIa-CRM 0.25 µg PSIb-CRM 0.25 µg PSIII-CRM 0.25 µg | Alum 400 µg | 8 |
| 7 | No antigen (1) | Alum 2 mg/ml | s.c. 200 µl | — | Alum 400 µg | 8 |
| 8 | No antigen (2) | Alum 2 mg/ml | s.c. 200 µl | — | Alum 400 µg | 8 |

Figure 4:
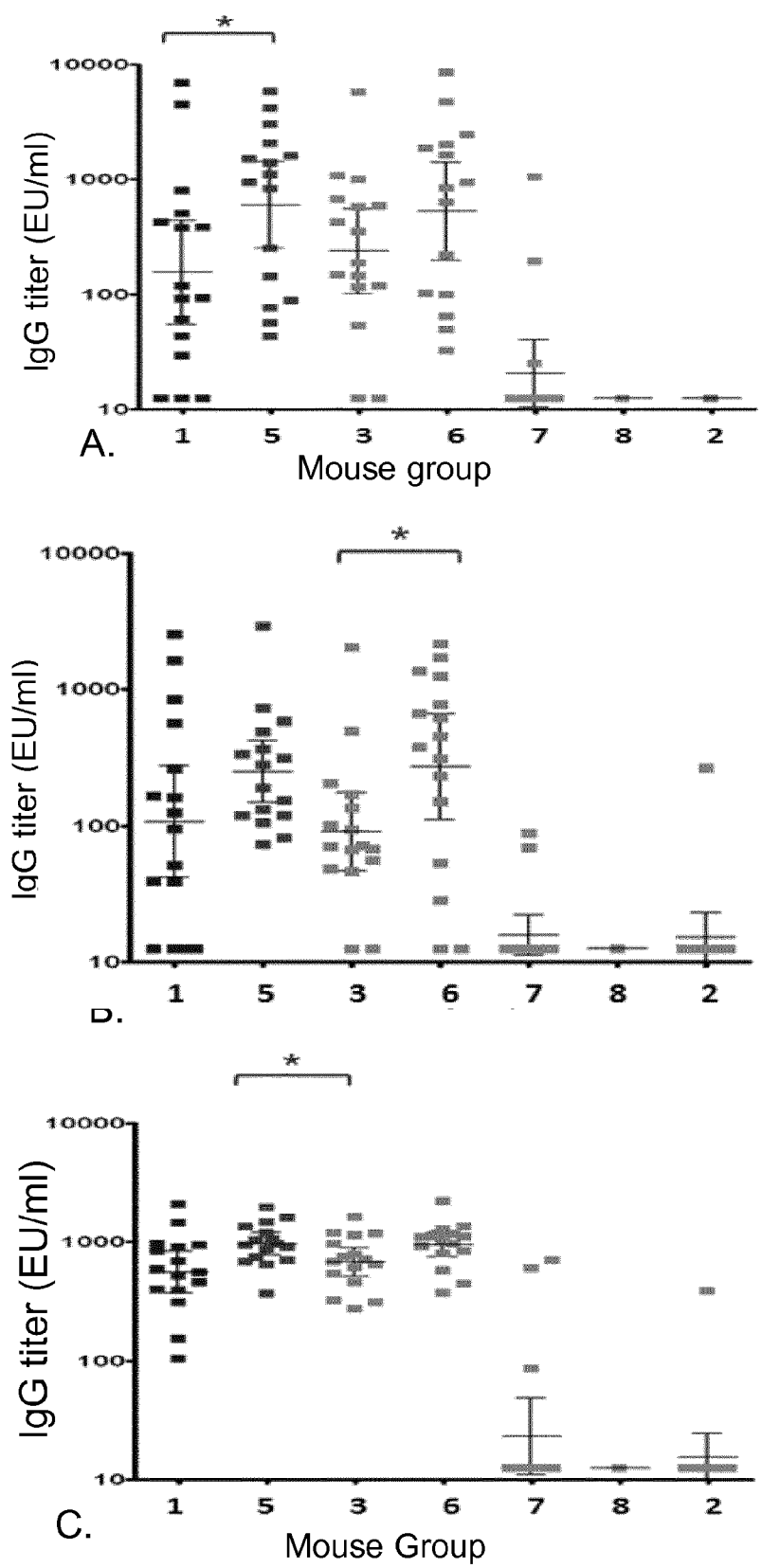
FIG. 4 shows IgG titers against (A) GBS Ia, (B) GBS Ib and (C) GBS III in mouse groups described in Table 3. Statistical significance is indicated by * ($p<0.05$). GMT titers are indicated by the central bar. Upper and lower bars indicate 95% confidence intervals.
Figure 5:
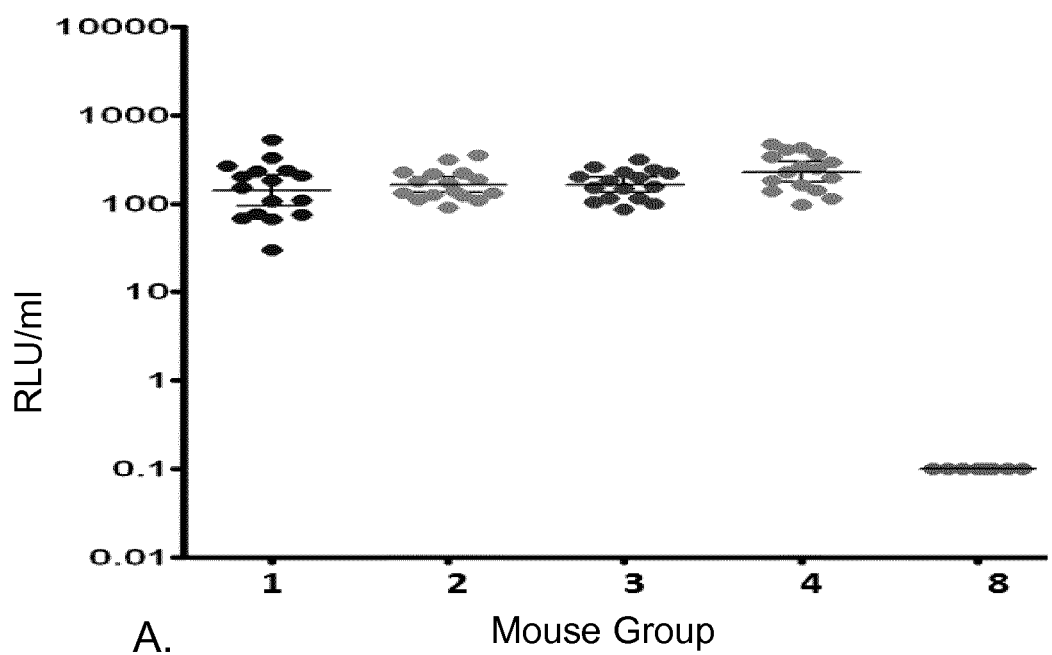
FIG. 5 shows IgG titers against (A) Diptheria Toxoid, (B) Tetanus Toxoid, (C) Pertussis Toxoid, (D) Pertussis FHA and (E) Pertussis 69K in mouse groups described in Table 3. Statistical significance is indicated by ** ($p<0.01$) and * ($p<0.05$). GMT titers are indicated by the central bar. Upper and lower bars indicate 95% confidence intervals.
Figure 5:
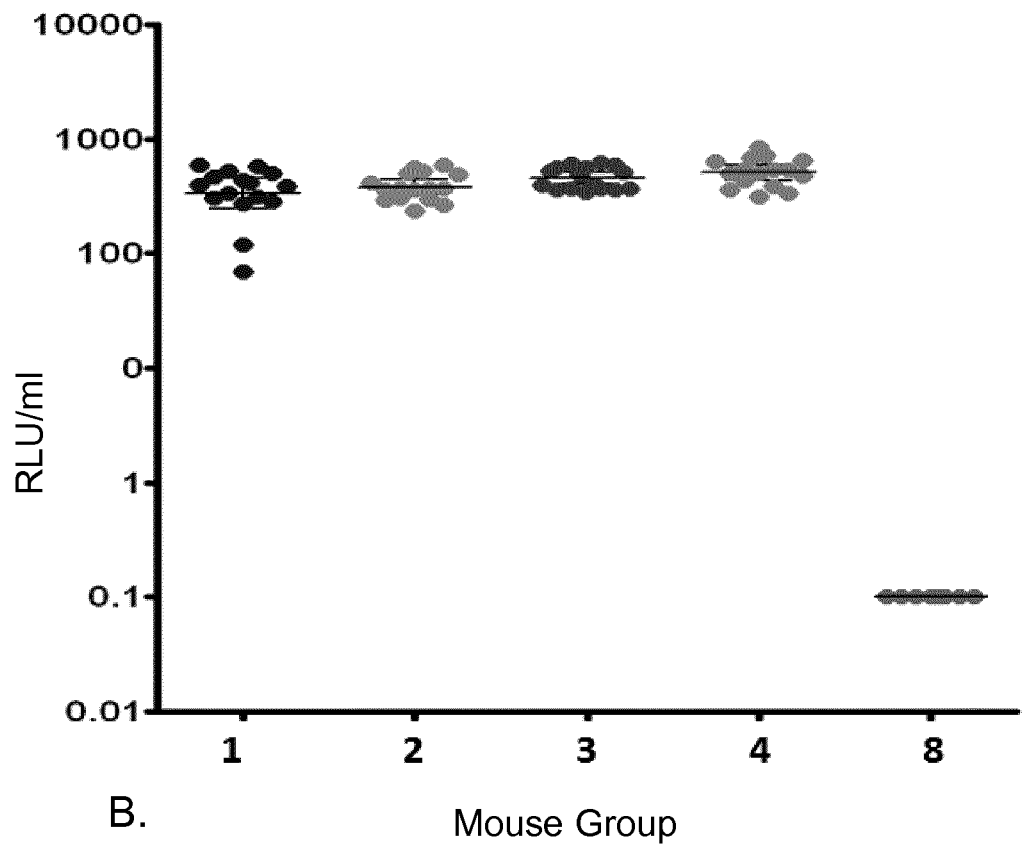
Figure 5:
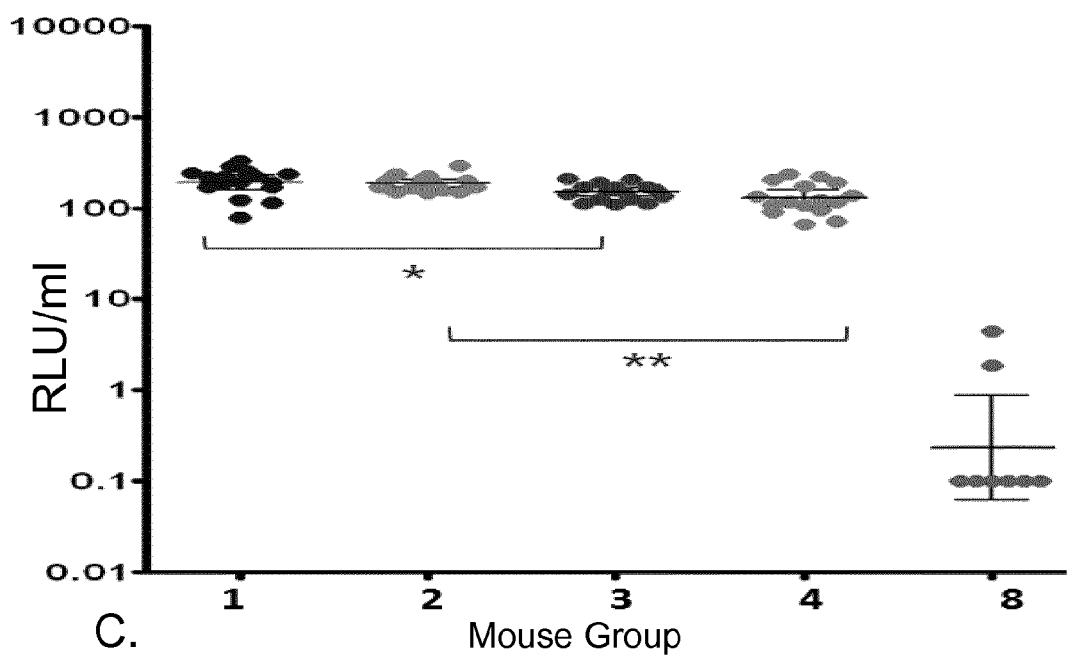
Figure 5:
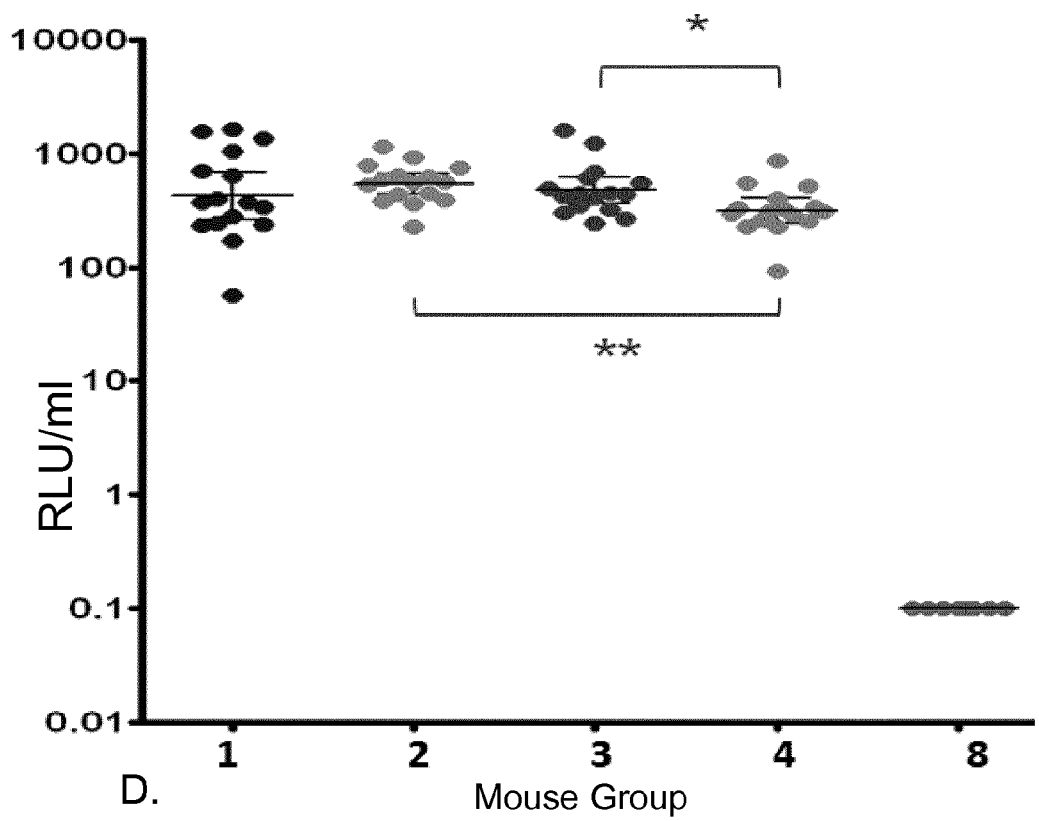
Figure 5:
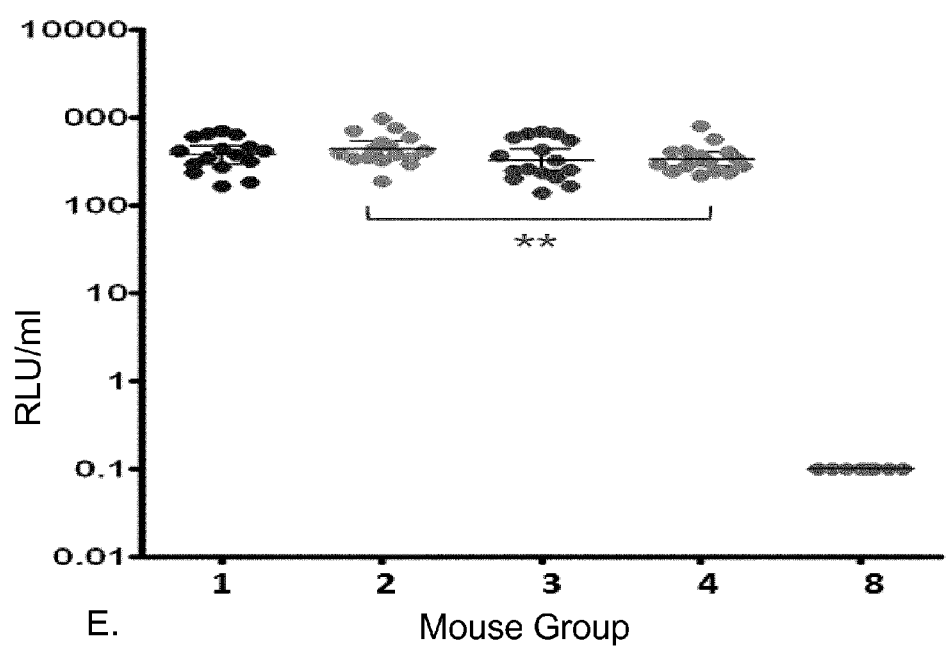

FIGS. 4 and 5 show the IgG titers against the various antigens for all groups after 3 immunizations for the groups of mice tested in study 2. The GMT titers are indicated in Table 4 below.

TABLE 4

GMT serum IgG titers after 3 immunizations in mice tested in study 2.

| | Group 1 | Group 2 | Group 3 | Group 4 | Group 5 | Group 6 | Group 7 | Group 8 |
|---|---|---|---|---|---|---|---|---|
| GBS Ia | 155.5 | 12.5 | 237.0 | N/A | 598.6 | 418.3 | 20.4 | 12.5 |
| GBS Ib | 107.5 | 15.1 | 90.6 | N/A | 250.4 | 271.7 | 15.7 | 12.5 |
| GBS III | 588.2 | 12.5 | 677.7 | N/A | 958.9 | 946.4 | 23.1 | 12.5 |
| DT | 141.3 | 164.3 | 164.5 | 228.2 | N/A | N/A | N/A | 0.1 |
| TT | 333.6 | 382.1 | 457.2 | 509.6 | N/A | N/A | N/A | 0.1 |
| PT | 191.4 | 187.1 | 149.9 | 128.1 | N/A | N/A | N/A | 0.2 |
| FHA | 423.8 | 544.6 | 476.1 | 314.9 | N/A | N/A | N/A | 0.1 |
| 69K | 374.7 | 435.4 | 328.2 | 337.9 | N/A | N/A | N/A | 0.1 |

For IgG titers post 3rd immunization against GBS Ia, Ib and III, the first observation is that two mice from group 7 probably received vaccine by mistake (high IgG titers to all three antigens, never observed previously in similar placebo groups). Secondly, a trend of lower IgG titers to all three GBS antigens in the groups reconstituted with TdaP (2-4 fold GMT, P<0.05 in some of the cases) compared to GBS vaccines without TdaP was observed. The same trend was observed for post-2 IgG titers to all serotypes.

For IgG titers post 3rd immunization against DT, TT, PT, FHA and 69K, respectively, no significant differences in the IgG responses between any of the groups were detected by Mann-Whitney test, indicating the complete absence of interference. No dose response was observed for DT and TT, while slightly higher titers were observed for higher doses compared to lower doses of pertussis PT, FHA and 69K antigens.

When the IgG titers against GBS Ia, Ib and III in groups 5 and 6, where responses to GBS 1 µg (high, L) and 0.25 µg (low, L) vaccine doses were compared, the variability in individual responses to GBS Ia and Ib was higher than that to GBS III. No significant differences between low and high doses were observed for any of the serotypes, while a lower number of non-responders and significantly higher responses at post-3 compared to post-2 were detected for all serotypes (Mann-Whitney U test).

Figure 6:
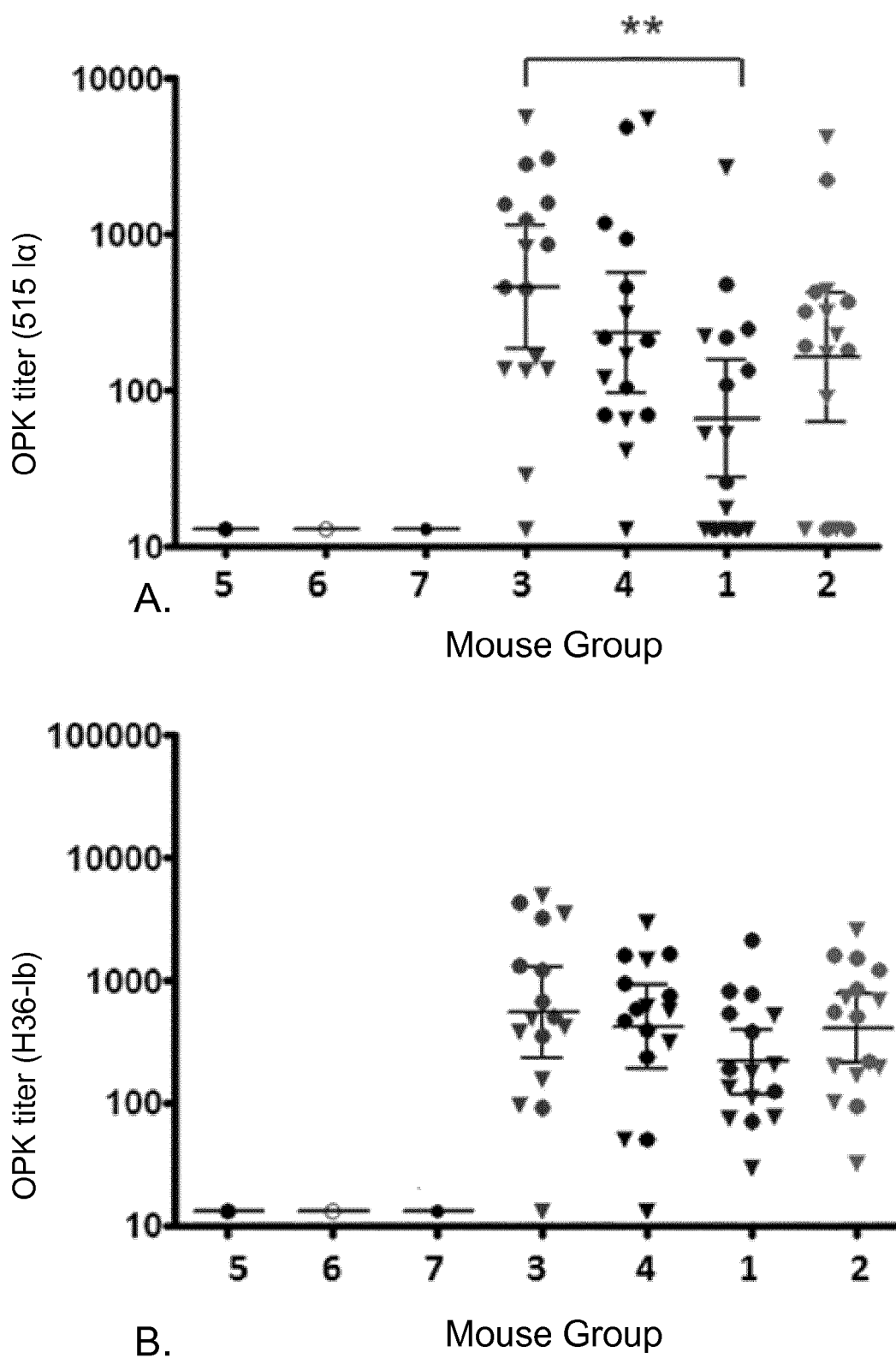
FIG. 6 shows OPK titers against (A) GBS Ia, (B) GBS Ib and (C) GBS III in mouse groups described in Table 3. Sera were pooled from all mice in each group for each experiment. GMT titers are indicated by the central bar.
Figure 6:
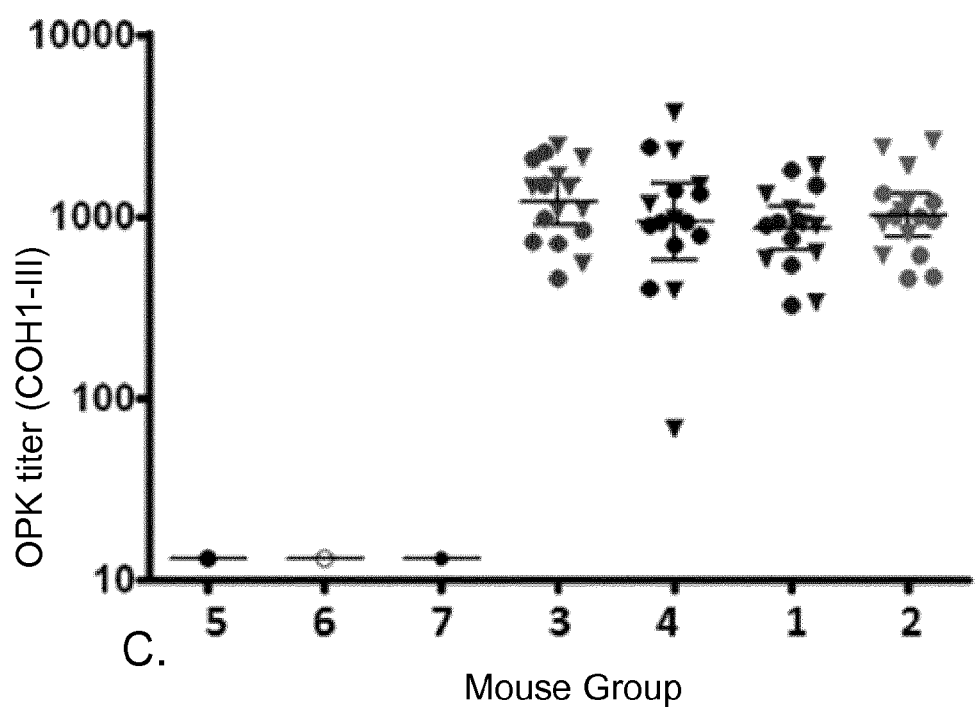

FIG. 6 shows the OPK titers against GBS Ia, Ib and III of the seven groups of mice tested in study 2. There is a trend of slightly lower titers in GBS vaccines formulated with TdaP compared to GBS alone.

Study 3: GBS Reconstituted in Tetanus and Tetanus/Diphteria Liquid Vaccines

This study investigated the immunogenicity of lyophilized GBS trivalent vaccines (Ia, Ib, III polysaccharides conjugated to CRM197) reconstituted with Alum adjuvanted liquid vaccines containing (i) Tetanus antigen or (ii) Tetanus and Diphtheria antigens.

The immunization protocol is reported in Table 5 and was repeated two times.

In each protocol, seven groups of 8 CD1 female mice were immunized subcutaneously on days 0 and 21 with 2 doses of the vaccines shown in Table 5, and bled on days 0 and 35.

TABLE 5

Immunization protocol for study 3.

| Group N° | Vaccine Type | Vaccine composition | Volume route | Antigens Dose | Adjuvant Dose | N° mice |
|---|---|---|---|---|---|---|
| 1 | GBS + T | PSIa-CRM 5 µg/ml<br>PSIb-CRM 5 µg/ml<br>PSIII-CRM 5 µg/ml<br>T 40 Ul/ml<br>Alum 3 mg/ml | s.c.<br>200 µl | PSIa-CRM 1 µg<br>PSIb-CRM 1 µg<br>PSIII-CRM 1 µg<br>T 8 Ul | Alum<br>600 µg | 8 |
| 2 | GBS + TD | PSIa-CRM 5 µg/ml<br>PSIb-CRM 5 µg/ml<br>PSIII-CRM 5 µg/ml<br>T 40 Ul/ml<br>D 4 µg/ml<br>Alum 3 mg/ml | s.c.<br>200 µl | PSIa-CRM 1 µg<br>PSIb-CRM 1 µg<br>PSIII-CRM 1 µg<br>T 8 Ul<br>D 0.8 Ul | Alum<br>600 µg | 8 |
| 3 | GBS only (1) | PSIa-CRM 5 µg/ml<br>PSIb-CRM 5 µg/ml<br>PSIII-CRM 5 µg/ml<br>Alum 3 mg/ml | s.c.<br>200 µl | PSIa-CRM 1 µg<br>PSIb-CRM 1 µg<br>PSIII-CRM 1 µg | Alum<br>600 µg | 8 |
| 4 | GBS only (2) | PSIa-CRM 5 µg/ml<br>PSIb-CRM 5 µg/ml<br>PSIII-CRM 5 µg/ml<br>Alum 3 mg/ml | s.c.<br>200 µl | PSIa-CRM 1 µg<br>PSIb-CRM 1 µg<br>PSIII-CRM 1 µg | Alum<br>600 µg | 8 |
| 5 | No antigen | Alum 3 mg/ml | s.c.<br>200 µl | — | Alum<br>600 µg | 8 |
| 6 | T only | T 40 Ul/ml<br>Alum 3 mg/ml | s.c.<br>200 µl | T 8 Ul | Alum<br>600 µg | 8 |
| 7 | TD only | T 40 Ul/ml<br>D 4 Ul/ml<br>Alum 3 mg/ml | s.c.<br>200 µl | T 8 Ul<br>D 0.8 Ul | Alum<br>600 µg | 8 |

Figure 7:
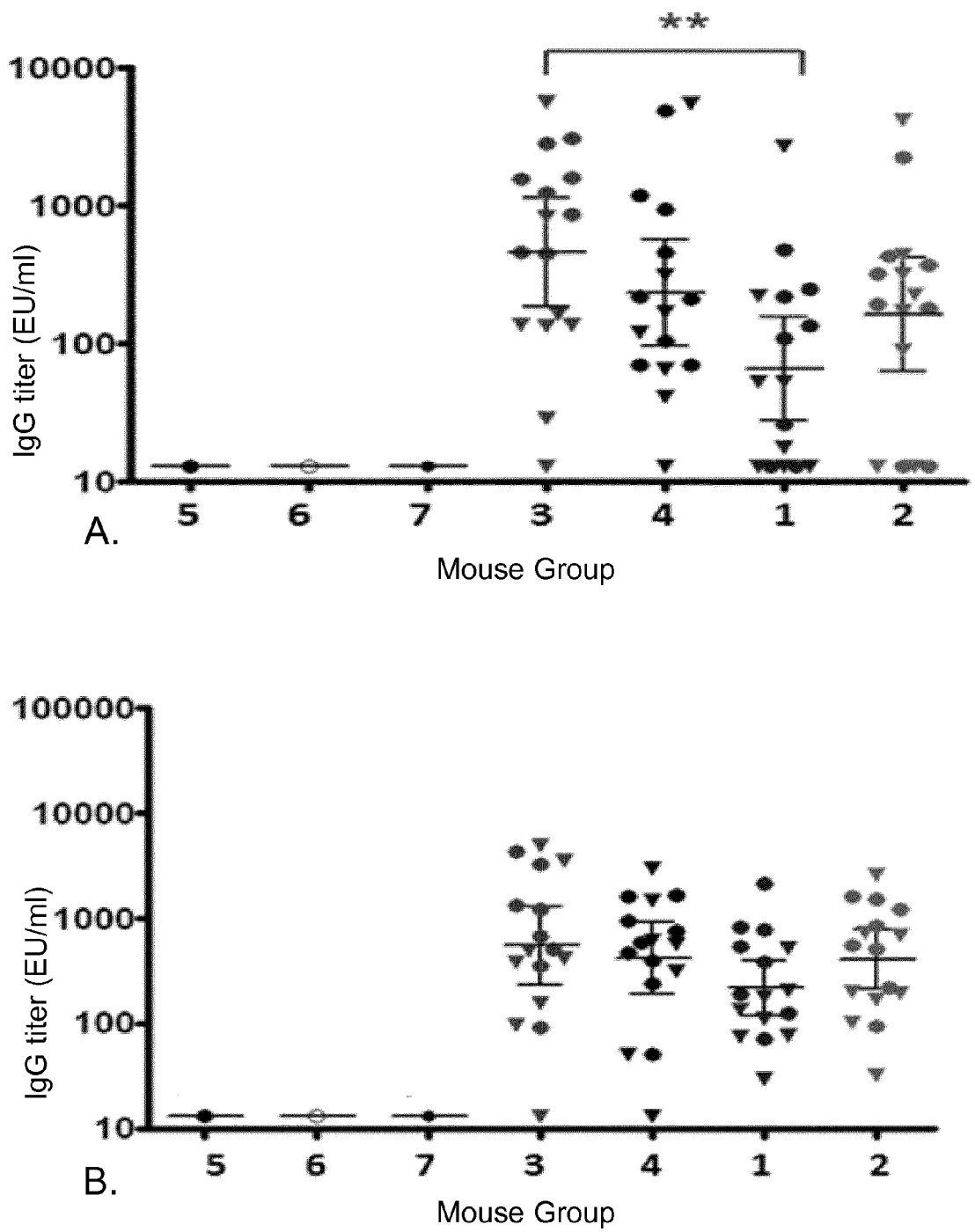
FIG. 7 shows IgG titers against (A) GBS Ia, (B) GBS Ib and (C) GBS III in mouse groups described in Table 5. Sera were pooled for groups 5, 6 and 7. Statistical significance is indicated by ** ($p<0.01$). GMT titers are indicated by the central bar. Upper and lower bars indicate 95% confidence intervals.
Figure 7:
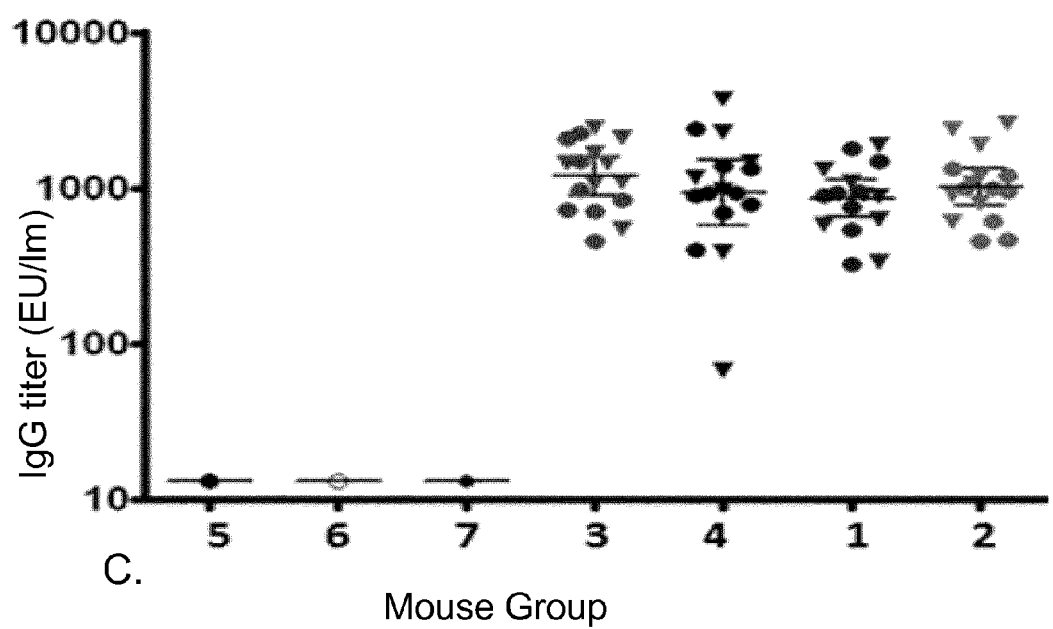
Figure 8:
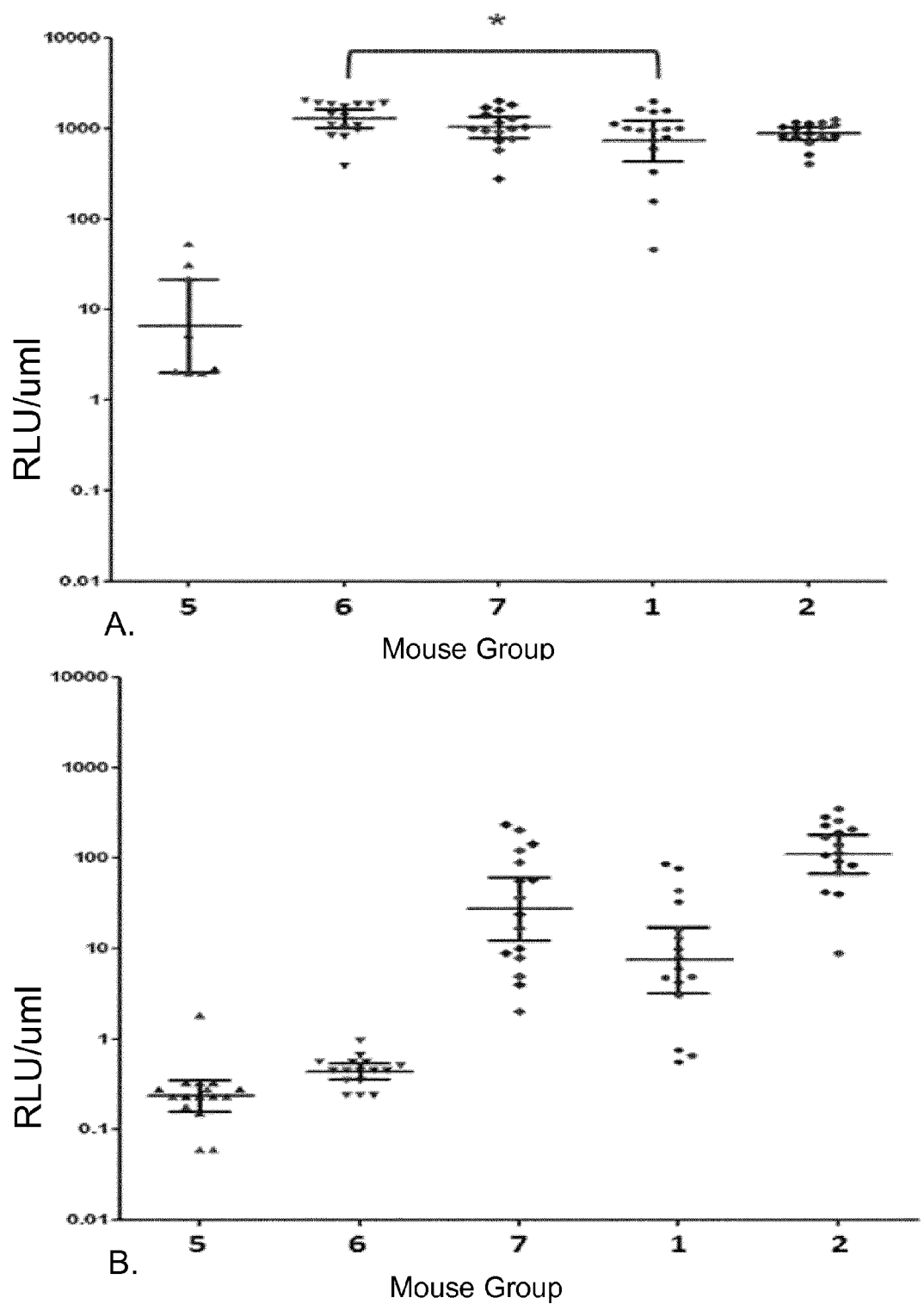
FIG. 8 shows IgG titers against (A) Tetanus Toxoid and (B) Diptheria Toxoid in mouse groups described in Table 5. Statistical significance is indicated by * ($p<0.05$). GMT titers are indicated by the central bar. Upper and lower bars indicate 95% confidence intervals.

FIGS. 7 and 8 show the IgG titers against the various antigens for all groups of mice tested in study 3 (merged results from 8+8 mice from the two experiments). The GMT titers are indicated in Table 6 below.

TABLE 6

GMT serum IgG titers after 2 immunizations in mice tested in study 3.

| | Group 1 | Group 2 | Group 3 | Group 4 | Group 5 | Group 6 | Group 7 |
|---|---|---|---|---|---|---|---|
| GBS Ia | 65 | 162 | 458 | 235 | 13 | 13 | 13 |
| GBS Ib | 217 | 402 | 550 | 417 | 13 | 13 | 13 |
| GBS III | 854 | 1018 | 1186 | 924 | 13 | 13 | 13 |
| TT | 742.00 | 882.70 | N/A | N/A | 6.60 | 1295.00 | 1038.00 |
| DT | 7.49 | 111.6 | N/A | N/A | <LLOQ | <LLOQ | 28.52 |

<LLOQ = below lower limit of quantification

For the IgG titers against GBS Ia, Ib and III measured by ELISA, the Mann-Whitney test did not reveal any significant difference between vaccine groups, except for serotype Ia, where the vaccine constituted by GBS alone (group 3) yielded significantly higher titers than the one containing GBS plus Tetanus Toxoid. In the OPK assay, no major differences in OPK titers against GBS Ia, Ib or III (in the range of assay and biological variability) were detected for any of the vaccine formulations.

IgG titers against TT were significantly lower (P=0.03) in the group containing the GBS vaccine and TT compared to TT alone, although the difference in GMT titers was less than 2 fold. Concerning IgG responses to DT, they were higher in groups containing the GBS vaccine, as expected by the effect of CRM197 (detoxified DT).

Figure 9:
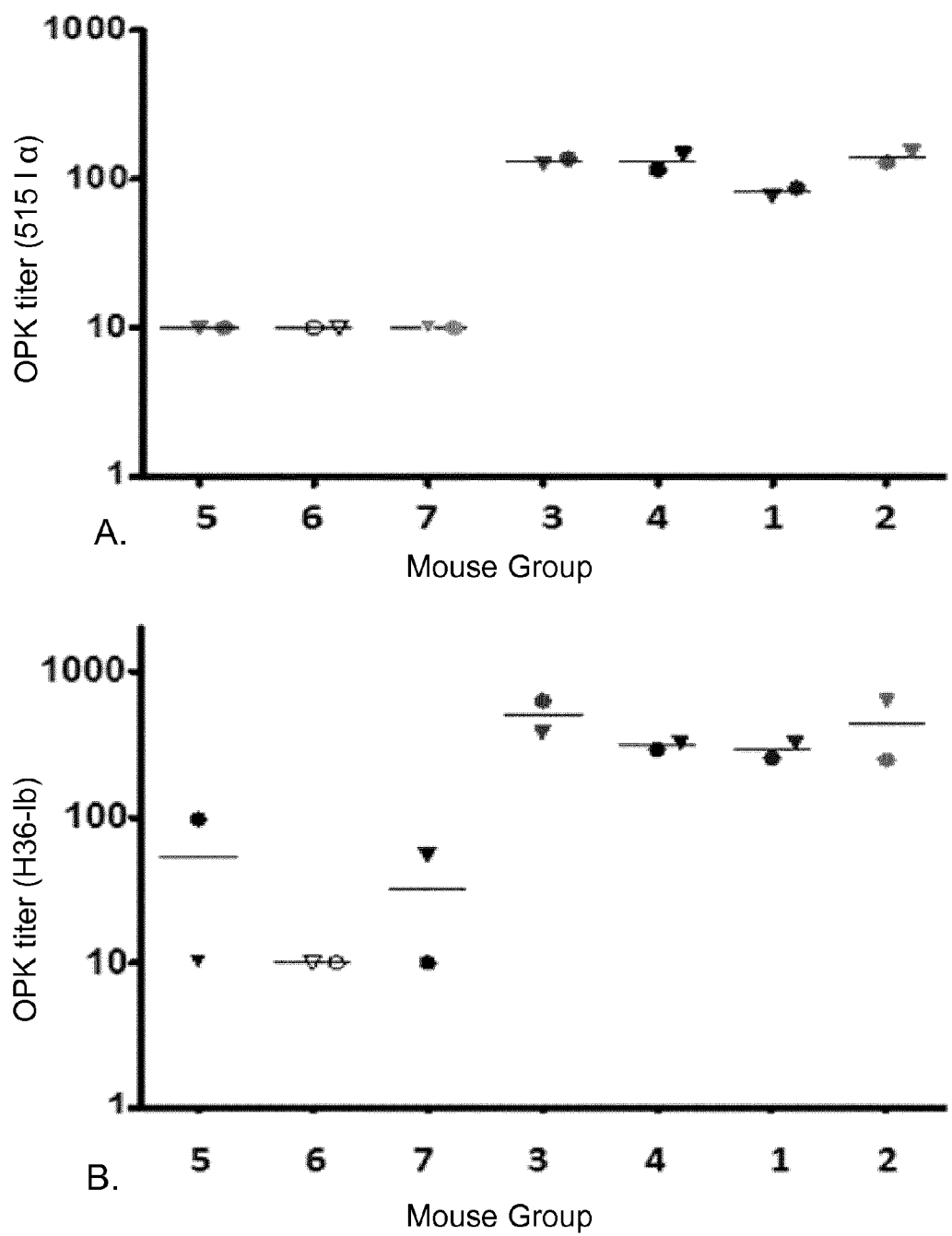
FIG. 9 shows OPK titers against (A) GBS Ia, (B) GBS Ib and (C) GBS III in mouse groups described in Table 5. Sera were pooled from all mice in each group for each experiment. GMT titers are indicated by the central bar.
Figure 9:
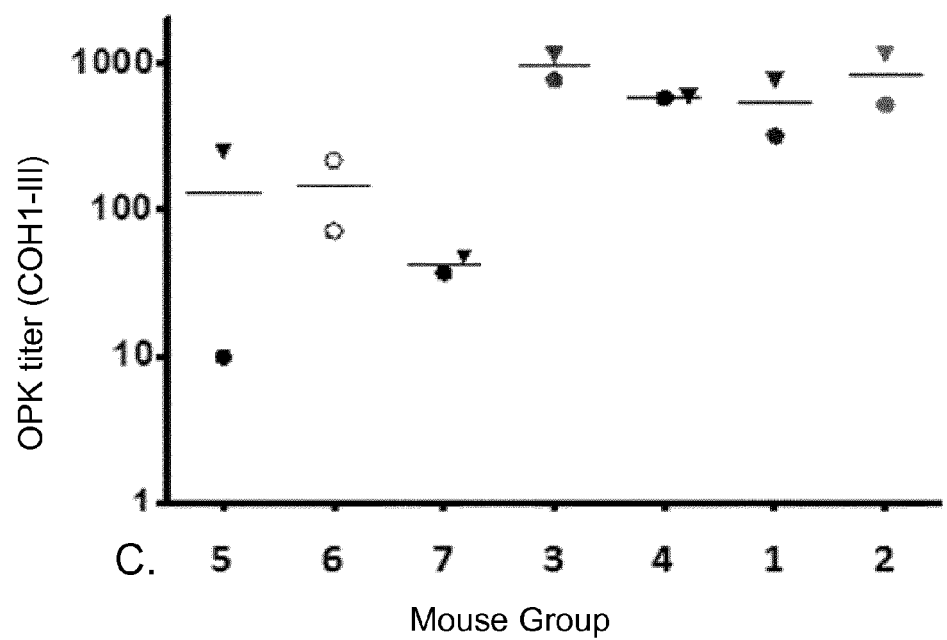

FIG. 9 shows the OPK titers against GBS Ia, Ib and III in sera from all groups of mice tested in study 3. As shown, no major differences in OPK titers against GBS Ia, Ib or III (in the range of assay and biological variability) were detected for any of the vaccine formulations.

CONCLUSIONS

The following observations were made regarding the immunogenicity of the investigated vaccine formulations:

GBS trivalent, Diphtheria, Tetanus and Pertussis vaccines elicited specific antibody titers to the corresponding antigens, in mice immunized with all of the investigated formulations.

Immunological interference between GBS and Tetanus/Diphteria/Pertussis/Polio vaccine combinations was investigated in studies 1 (intraperitoneal immunization with 2 vaccine doses) and 2 (subcutaneous immunization with 2 and 3 vaccine doses). No interference was observed in study 1, where IgG and functional antibody responses to GBS, Diphtheria, Tetanus and Pertussis antigens where comparable irrespective of their use, alone or in combination. In study 2, we observed a trend of lower IgG titers to all three GBS antigens reconstituted in TdaP compared to GBS alone, even though the differences in GMT titers were never higher than 4 fold.

Immunological interference between GBS and Tetanus or Tetanus/Diphteria vaccines was investigated in study 3. The Mann-Whitney test did not reveal significant differences in GBS responses between any of the vaccine groups except for serotype Ia, where the vaccine constituted by GBS alone yielded significantly higher titers than the one containing GBS plus Tetanus Toxoid. The same study revealed a slight interference of the GBS vaccine towards TT (2 fold GMT difference, P=0.03 for the difference in the IgG titers against TT, in the group containing the GBS vaccine compared to TT alone). Concerning IgG responses to DT, they were higher in groups containing the GBS vaccine, as expected by the effect of CRM197 (detoxified DT).

In conclusion, there was no evidence of strong interference between any of the investigated vaccines.

It will be understood that the invention has been described by way of example only and modifications may be made whilst remaining within the scope and spirit of the invention.

REFERENCES

[1] *Vaccines.* (eds. Plotkin & Orenstein). 4th edition, 2004, ISBN: 0-7216-9688-0.
[2] Paoletti et al. (1990) *J Biol Chem* 265:18278-83.
[3] Wessels et al. (1990) *J Clin Invest* 86:1428-33.
[4] Paoletti et al. (1992) *Infect Immun* 60:4009-14.
[5] Paoletti et al. (1992) *J Clin Invest* 89:203-9.
[6] Wessels et al. (1987) *Proc Natl Acad Sci USA* 84:9170-4.
[7] Wang et al. (2003) *Vaccine* 21:1112-7.
[8] Wessels et al. (1993) *Infect Immun* 61:4760-6
[9] Wessels et al. (1995) *J Infect Dis* 171:879-84.
[10] Baker et al. (2004) *J Infect Dis* 189:1103-12.
[11] Paoletti & Kasper (2003) *Expert Opin Biol Ther* 3:975-84.
[12] WO2012/035519
[13] WO2006/050341
[14] Guttormsen et al. (2008) Proc Natl Acad Sci USA. 105 (15):5903-8. Epub 2008 Mar. 31.
[15] WO96/40795
[16] Michon et al. (2006) Clin Vaccine Immunol. 2006 August; 13 (8):936-43.
[17] U.S. Pat. Nos. 6,027,733 & 6,274,144.
[18] www.polymer.de
[19] Lewis et al. (2004) *PNAS USA* 101:11123-8.
[20] Wessels et al. (1989) *Infect Immun* 57:1089-94.
[21] WO2006/082527.
[22] U.S. patent application 61/008,941, entitled "FERMENTATION PROCESSES FOR CULTIVATING STREPTOCOCCI AND PURIFICATION PROCESSES FOR OBTAINING CPS THEREFROM" filed on 20 Dec. 2007 and international patent application WO 2009/081276.
[23] Ramsay et al. (2001) *Lancet* 357 (9251):195-196.
[24] Lindberg (1999) *Vaccine* 17 Suppl 2:S28-36.
[25] Buttery & Moxon (2000) *J R Coll Physicians Lond* 34:163-68.
[26] Ahmad & Chapnick (1999) *Infect Dis Clin North Am* 13:113-33, vii.
[27] Goldblatt (1998) *J Med. Microbiol.* 47:563-7.
[28] European patent 0477508.
[29] U.S. Pat. No. 5,306,492.
[30] WO98/42721.
[31] Dick et al. in *Conjugate Vaccines* (eds. Cruse et al.) Karger, Basel, 1989, 10:48-114.
[32] Hermanson *Bioconjugate Techniques*, Academic Press, San Diego (1996) ISBN: 0123423368.
[33] U.S. Pat. No. 4,356,170.
[34] WO2006/082530.
[35] WO2005/000346
[36] Anonymous (January 2002) *Research Disclosure*, 453077.
[37] Anderson (1983) *Infect Immun* 39 (1):233-238.
[38] Anderson et al. (1985) *J Clin Invest* 76 (1):52-59.
[39] EP-A-0372501.
[40] EP-A-0378881.
[41] EP-A-0427347.
[42] WO93/17712
[43] WO94/03208.
[44] WO98/58668.
[45] EP-A-0471177.
[46] WO91/01146
[47] Falugi et al. (2001) *Eur J Immunol* 31:3816-24.
[48] Baraldo et al. (2004) *Infect Immun* 72:4884-87.
[49] EP-A-0594610.
[50] WO00/56360.
[51] WO02/091998.
[52] Kuo et al. (1995) *Infect Immun* 63:2706-13.
[53] WO01/72337
[54] WO00/61761.
[55] WO00/33882
[56] WO2004/041157.
[57] WO99/42130.
[58] WO2004/011027.
[59] WO96/40242.
[60] Lei et al. (2000) *Dev Biol (Basel)* 103:259-264.
[61] WO00/38711; U.S. Pat. No. 6,146,902.
[62] International patent application PCT/IB2008/02690, 'CONJUGATE PURIFICATION', claiming priority from GB-0713880.3 (NOVARTIS AG), published as WO 2009/010877.
[63] *Vaccines.* (eds. Plotkin & Orenstein). 4th edition, 2004, ISBN: 0-7216-9688-0.
[64] *National Institute for Biological Standards and Control*; Potters Bar, UK. www.nibsc.ac.uk
[65] Sesardic et al. (2001) *Biologicals* 29:107-22.
[66] NIBSC code: 98/560.
[67] Module 1 of WHO's *The immunological basis for immunization series* (Galazka).
[68] NIBSC code: 69/017.
[69] NIBSC code: DIFT.
[70] *National Institute for Biological Standards and Control*; Potters Bar, UK. www.nibsc.ac.uk
[71] Sesardic et al. (2002) *Biologicals* 30:49-68.
[72] NIBSC code: 98/552.
[73] Module 1 of WHO's *The immunological basis for immunization series* (Galazka).
[74] NIBSC code: TEFT.
[75] NIBSC code: 66/303.
[76] Rappuoli et al. (1991) *TIBTECH* 9:232-238.
[77] Module 6 of WHO's *The immunological basis for immunization series* (Robertson)
[78] WO2008/028956
[79] WO2008/028957
[80] Liao et al. (2012) *J Infect Dis.* 205:237-43
[81] Paoletti et al. (2001) *Vaccine* 19:2118-2126.
[82] WO00/56365.
[83] Gennaro (2000) *Remington: The Science and Practice of Pharmacy.* 20th edition, ISBN: 0683306472.
[84] WO01/41800.
[85] Paoletti (2001) *Vaccine* 19 (15-16):2118-26.
[86] WO03/009869.
[87] Almeida & Alpar (1996) *J Drug Targeting* 3:455-467.
[88] Agarwal & Mishra (1999) *Indian J Exp Biol* 37:6-16.
[89] WO00/53221.
[90] Jakobsen et al. (2002) *Infect Immun* 70:1443-1452.
[91] Bergquist et al. (1998) *APMIS* 106:800-806.
[92] Baudner et al. (2002) *Infect Immun* 70:4785-4790.
[93] Ugozzoli et al. (2002) *J Infect Dis* 186:1358-1361.
[94] Nony et al. (2001) *Vaccine* 27:3645-51.
[95] U.S. Pat. No. 6,355,271.
[96] WO00/23105.
[97] *Vaccine Design* . . . (1995) eds. Powell & Newman. ISBN: 030644867X. Plenum.
[98] U.S. Pat. No. 5,057,540.
[99] WO96/33739.
[100] EP-A-0109942.
[101] WO96/11711.

[102] WO00/07621.
[103] Barr et al. (1998) *Advanced Drug Delivery Reviews* 32:247-271.
[104] Sjolanderet et al. (1998) *Advanced Drug Delivery Reviews* 32:321-338.
[105] Niikura et al. (2002) *Virology* 293:273-280.
[106] Lenz et al. (2001) *J Immunol* 166:5346-5355.
[107] Pinto et al. (2003) *J Infect Dis* 188:327-338.
[108] Gerber et al. (2001) *Virol* 75:4752-4760.
[109] WO03/024480
[110] WO03/024481
[111] Gluck et al. (2002) *Vaccine* 20:B10-B16.
[112] Kandimalla et al. (2003) *Nucleic Acids Research* 31:2393-2400.
[113] WO02/26757.
[114] WO99/62923.
[115] Krieg (2003) *Nature Medicine* 9:831-835.
[116] McCluskie et al. (2002) *FEMS Immunology and Medical Microbiology* 32:179-185.
[117] WO98/40100.
[118] U.S. Pat. No. 6,207,646.
[119] U.S. Pat. No. 6,239,116.
[120] U.S. Pat. No. 6,429,199.
[121] Kandimalla et al. (2003) *Biochemical Society Transactions* 31 (part 3):654-658.
[122] Blackwell et al. (2003) *J Immunol* 170:4061-4068.
[123] Krieg (2002) *Trends Immunol* 23:64-65.
[124] WO01/95935.
[125] Kandimalla et al. (2003) *BBRC* 306:948-953.
[126] Bhagat et al. (2003) *BBRC* 300:853-861.
[127] WO03/035836.
[128] WO95/17211.
[129] WO98/42375.
[130] Beignon et al. (2002) *Infect Immun* 70:3012-3019.
[131] Pizza et al. (2001) *Vaccine* 19:2534-2541.
[132] Pizza et al. (2000) *Int J Med Microbiol* 290:455-461.
[133] Scharton-Kersten et al. (2000) *Infect Immun* 68:5306-5313.
[134] Ryan et al. (1999) *Infect Immun* 67:6270-6280.
[135] Partidos et al. (1999) *Immunol Lett* 67:209-216.
[136] Peppoloni et al. (2003) *Expert Rev Vaccines* 2:285-293.
[137] Pine et al. (2002) *J Control Release* 85:263-270.
[138] Domenighini et al. (1995) *Mol Microbiol* 15:1165-1167.
[139] WO99/40936.
[140] WO99/44636.
[141] Singh et al] (2001) *J Cont Release* 70:267-276.
[142] WO99/27960.
[143] U.S. Pat. No. 6,090,406
[144] U.S. Pat. No. 5,916,588
[145] EP-A-0626169.
[146] WO99/52549.
[147] WO01/21207.
[148] WO01/21152.
[149] Andrianov et al. (1998) *Biomaterials* 19:109-115.
[150] Payne et al. (1998) *Adv Drug Delivery Review* 31:185-196.
[151] Stanley (2002) *Clin Exp Dermatol* 27:571-577.
[152] Jones (2003) *Curr Opin Investig Drugs* 4:214-218.
[153] WO04/60308
[154] WO04/64759.
[155] Hennings et al. (2001) J Infect Dis. 183 (7):1138-42. Epub 2001 Mar. 1.
[156] Glezen & Alpers (1999) *Clin. Infect. Dis.* 28:219-224
[157] Madoff et al. (1994) *J Clin Invest* 94:286-92.
[158] Paoletti et al. (1994) *Infect Immun* 62:3236-43.
[159] GB patent application no. 1121301.4
[160] Fabbrini et al. (2012) *J Immun Methods* 378:11-19

The invention claimed is:
1. An immunogenic composition comprising:
(A) a bacterial saccharide conjugate component comprising:
(i) a capsular saccharide from Group B *streptococcus* (GBS) serotype Ia conjugated to a carrier protein;
(ii) a capsular saccharide from GBS serotype Ib conjugated to a carrier protein;
(iii) a capsular saccharide from GBS serotype III conjugated to a carrier protein; and
(B) a protein antigen component consisting of:
(i) unconjugated tetanus toxoid (TT),
(ii) unconjugated diphtheria toxoid (DT), and
(iii) acellular pertussis antigens.
2. The immunogenic composition according to claim 1, wherein each GBS capsular saccharide is present at an amount from 0.1 to 30 μg per dose.
3. The immunogenic composition according to claim 1, wherein the conjugate that is a capsular saccharide from GBS serotype Ia conjugated to a carrier protein has a saccharide:protein ratio (w/w) between about 1:1 to 1:2; the conjugate that is a capsular saccharide from GBS serotype Ib conjugated to a carrier protein has a saccharide:protein ratio (w/w) between about 1:1 to 1:2; and the conjugate that is a capsular saccharide from GBS serotype III conjugated to a carrier protein has a saccharide:protein ratio (w/w) between about 3:1 to 1:1.
4. The immunogenic composition according to claim 1, wherein the carrier protein is a diphtheria toxoid, a tetanus toxoid or CRM197.
5. The immunogenic composition according to claim 4, further comprising a conjugate selected from: a conjugate that is a capsular saccharide from GBS serotype II conjugated to a carrier protein; and a conjugate that is a capsular saccharide from GBS serotype V conjugated to a carrier protein.
6. The immunogenic composition according to claim 1, wherein the acellular pertussis antigens consist of detoxified pertussis toxin, filamentous hemagglutinin and pertactin.
7. The immunogenic composition according to claim 1, wherein the unconjugated diphtheria toxoid is present at a concentration of between 4 Lf/ml and 8 Lf/ml per 0.5 ml dose.
8. The immunogenic composition according to claim 1, wherein the unconjugated tetanus toxoid is present at a concentration of about 5 Lf per 0.5 ml dose.
9. The immunogenic composition according to claim 4, wherein the immunogenic composition contains an aluminium salt adjuvant.
10. The immunogenic composition according to claim 4, wherein the composition is a vaccine.
11. The immunogenic composition according to claim 4, wherein the carrier protein for each GBS capsular saccharide is the same.
12. A method for raising an immune response in a patient, comprising the step of administering to the patient a composition according to claim 1.
13. A process for preparing the immunogenic composition according to claim 1, comprising mixing said bacterial capsular saccharide antigen component with said protein antigen component.
14. The process according to claim 13, wherein the GBS conjugates in the bacterial capsular saccharide antigen component are lyophilised.

15. A kit for preparing the immunogenic composition according to claim 1, comprising said bacterial capsular saccharide antigen component and said protein antigen component; wherein the two components are in separate containers.

* * * * *